United States Patent
Toth et al.

(10) Patent No.: US 10,470,684 B2
(45) Date of Patent: Nov. 12, 2019

(54) CONTROLLED SYMPATHECTOMY AND MICRO-ABLATION SYSTEMS AND METHODS

(71) Applicant: Autonomix Medical, Inc., Excelsior, MN (US)

(72) Inventors: Landy Toth, Doylestown, PA (US); Robert Schwartz, Inver Grove Heights, MN (US)

(73) Assignee: Autonomix Medical, INC., Ivyland, PA (US)

( * ) Notice: Subject to any disclaimer, the term of this patent is extended or adjusted under 35 U.S.C. 154(b) by 654 days.

(21) Appl. No.: 14/374,466

(22) PCT Filed: Jan. 25, 2013

(86) PCT No.: PCT/US2013/023157
§ 371 (c)(1),
(2) Date: Jul. 24, 2014

(87) PCT Pub. No.: WO2013/112844
PCT Pub. Date: Aug. 1, 2013

(65) Prior Publication Data
US 2015/0011843 A1    Jan. 8, 2015

Related U.S. Application Data

(60) Provisional application No. 61/613,097, filed on Mar. 20, 2012, provisional application No. 61/590,812, filed on Jan. 26, 2012.

(51) Int. Cl.
*A61B 5/053* (2006.01)
*A61B 5/00* (2006.01)
(Continued)

(52) U.S. Cl.
CPC .......... *A61B 5/0538* (2013.01); *A61B 5/0084* (2013.01); *A61B 5/01* (2013.01);
(Continued)

(58) Field of Classification Search
None
See application file for complete search history.

(56) References Cited

U.S. PATENT DOCUMENTS 6,024,739 A  *  2/2000  Ponzi ..................... A61B 18/24
                                                            600/374
7,255,695 B2     8/2007  Falwell et al.
(Continued)

FOREIGN PATENT DOCUMENTS

CN       101309651 A      11/2008
CN       102274074 A      12/2011
(Continued)

*Primary Examiner* — Linda C Dvorak
*Assistant Examiner* — Ryan T Clark
(74) *Attorney, Agent, or Firm* — Ryan, Mason & Lewis, LLP

(57) ABSTRACT

A microsurgical tool is configured for monitoring, evaluating, mapping, and/or modulating electrophysiological activity in the vicinity of a lumen within a body. The microsurgical tool may be part of a system used in evaluating the sympathetic tone of a subject and/or neuromodulating an anatomical site in the vicinity of a lumen within a body. Such systems include a catheter system for controlled sympathectomy procedures and/or controlled micro ablation procedures. Such systems may be used in methods for performing a controlled surgical procedure, including performing controlled surgical procedures in a minimally invasive manner.

24 Claims, 11 Drawing Sheets

(51) Int. Cl.
    *A61B 5/01*      (2006.01)
    *A61B 5/0492*    (2006.01)
    *A61B 5/1459*    (2006.01)
    *A61B 5/11*      (2006.01)
    *A61N 1/36*      (2006.01)
    *A61B 5/0488*    (2006.01)
    *A61B 18/14*     (2006.01)
    *A61B 18/00*     (2006.01)
    *A61N 7/00*      (2006.01)
    *A61B 90/00*     (2016.01)

(52) U.S. Cl.
    CPC .......... *A61B 5/0492* (2013.01); *A61B 5/1106* (2013.01); *A61B 5/1459* (2013.01); *A61B 5/6857* (2013.01); *A61B 5/6858* (2013.01); *A61B 5/6885* (2013.01); *A61N 1/36114* (2013.01); *A61N 1/36185* (2013.01); *A61B 5/04882* (2013.01); *A61B 5/4893* (2013.01); *A61B 18/1492* (2013.01); *A61B 2018/0016* (2013.01); *A61B 2018/00214* (2013.01); *A61B 2018/00345* (2013.01); *A61B 2018/00505* (2013.01); *A61B 2018/00577* (2013.01); *A61B 2018/00654* (2013.01); *A61B 2018/00839* (2013.01); *A61B 2018/1425* (2013.01); *A61B 2090/065* (2016.02); *A61B 2562/028* (2013.01); *A61B 2562/0261* (2013.01); *A61B 2562/06* (2013.01); *A61N 7/00* (2013.01)

(56)          References Cited

U.S. PATENT DOCUMENTS

| 7,283,866    | B2* | 10/2007 | Mumford ............ A61B 5/0492 |
|              |     |         |                          600/546 |
| 2002/0062146 | A1* | 5/2002  | Makower ........ A61B 17/00234 |
|              |     |         |                          623/1.13 |
| 2002/0072717 | A1* | 6/2002  | Mueller ............. A61B 17/3207 |
|              |     |         |                          604/212 |
| 2002/0107512 | A1* | 8/2002  | Edwards ........... A61B 18/1492 |
|              |     |         |                          606/41 |
| 2004/0193021 | A1* | 9/2004  | Zdeblick ............... A61B 5/036 |
|              |     |         |                          600/300 |
| 2005/0090728 | A1* | 4/2005  | Mest .................... A61B 5/0422 |
|              |     |         |                          600/373 |
| 2005/0234523 | A1  | 10/2005 | Levin et al. |
| 2007/0083239 | A1  | 4/2007  | Demarais et al. |
| 2007/0203549 | A1* | 8/2007  | Demarais ................. A61N 1/05 |
|              |     |         |                          607/72 |
| 2009/0069808 | A1  | 3/2009  | Pike, Jr. et al. |
| 2009/0275956 | A1  | 11/2009 | Burnes et al. |
| 2011/0106074 | A1  | 5/2011  | Kunis et al. |
| 2011/0257523 | A1  | 10/2011 | Hastings et al. |
| 2011/0264086 | A1  | 10/2011 | Ingle |
| 2011/0306851 | A1* | 12/2011 | Wang .................. A61B 5/4893 |
|              |     |         |                          600/301 |
| 2011/0307034 | A1  | 12/2011 | Hastings et al. |

FOREIGN PATENT DOCUMENTS

| EP | 0145166         | A2  | 10/1984 |           |
| EP | 1799302         | B1  | 6/2007  |           |
| EP | 2092957         | A1  | 8/2009  |           |
| EP | 2218479         | A2  | 8/2010  |           |
| EP | 13741227.6-1657 |     | 1/2016  |           |
| ES | 2361583         | T3  | 6/2011  |           |
| JP | H07507709       | A   | 8/1995  |           |
| JP | 2003510160      | A   | 3/2003  |           |
| JP | 2003514612      | A   | 4/2003  |           |
| JP | 2006509547      | A   | 3/2006  |           |
| JP | 2010155083      | A   | 7/2010  |           |
| JP | 2017-232401     |     | 9/2018  |           |
| WO | 2006022790      | A1  | 3/2006  |           |
| WO | 2009073223      | A1  | 6/2009  |           |
| WO | 2011075328      | A1  | 6/2011  |           |
| WO | WO 2011075328   | A1* | 6/2011  | ........... A61B 5/0215 |
| WO | PCT/US2013/023157 |   | 4/2013  |           |

* cited by examiner

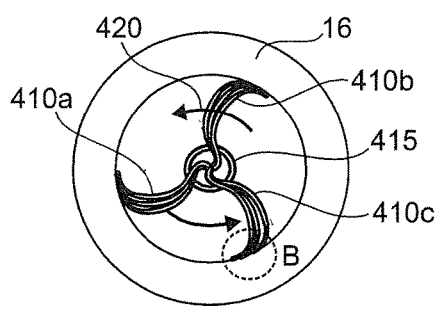
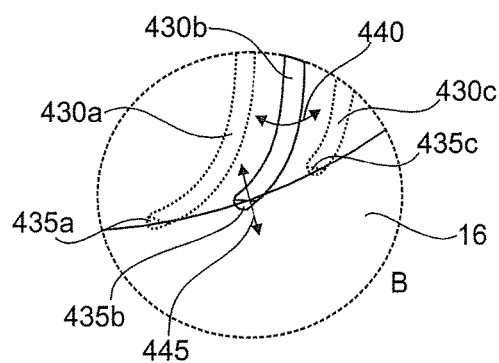
Fig 4a  Fig 4b
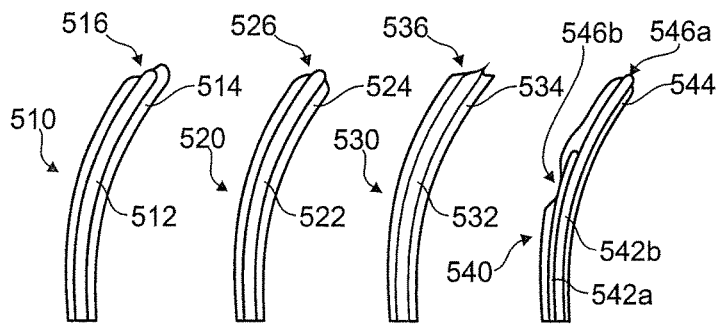
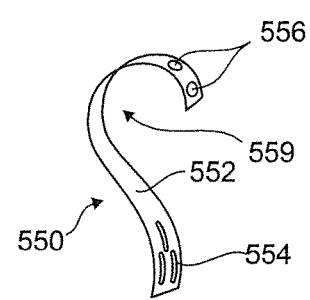
Fig 5a  Fig 5b
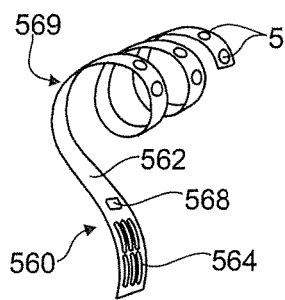
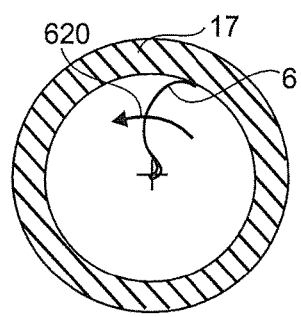
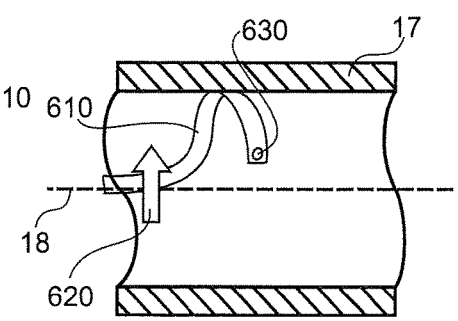
Fig 5c  Fig 6a  Fig 6b

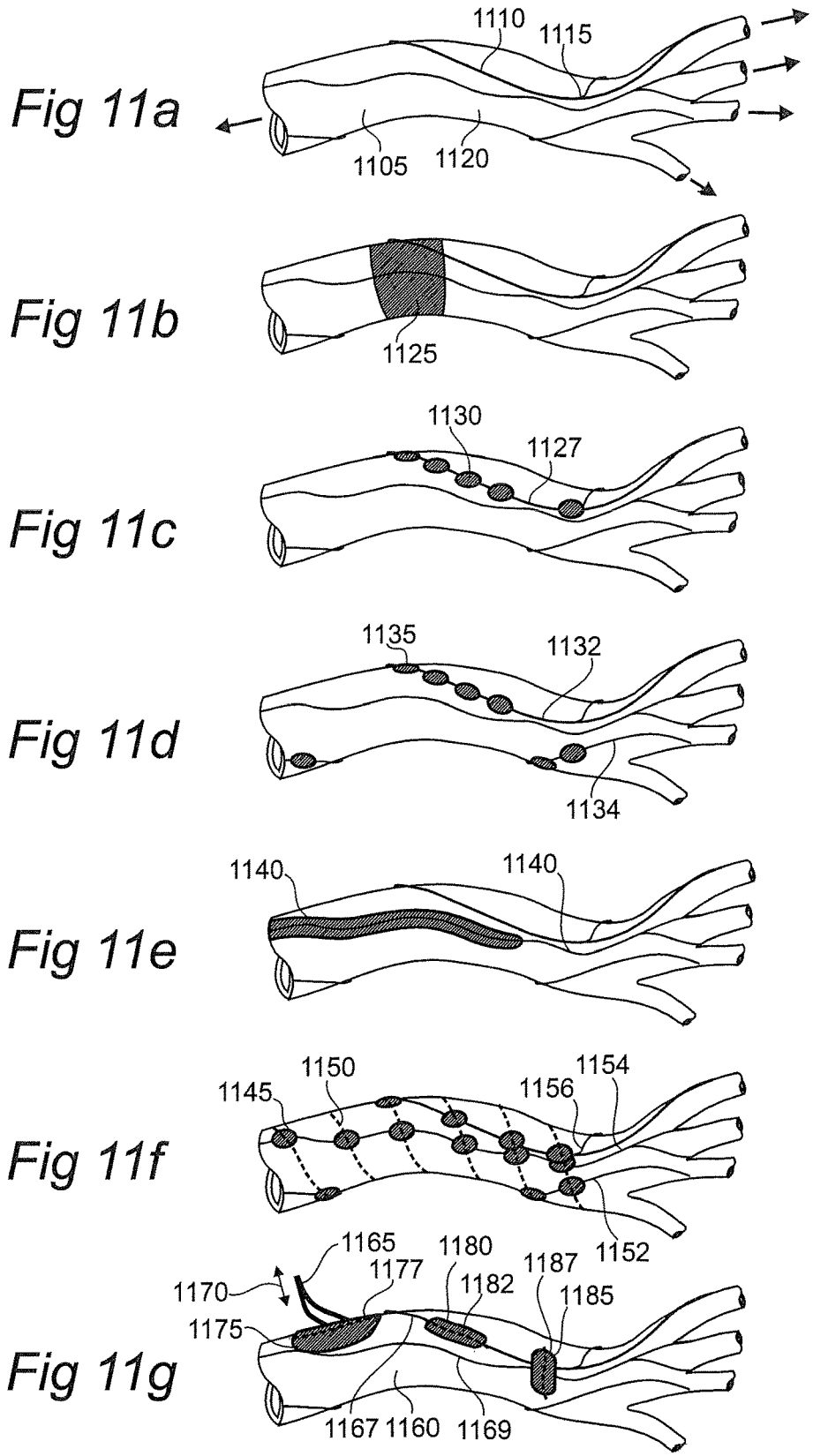

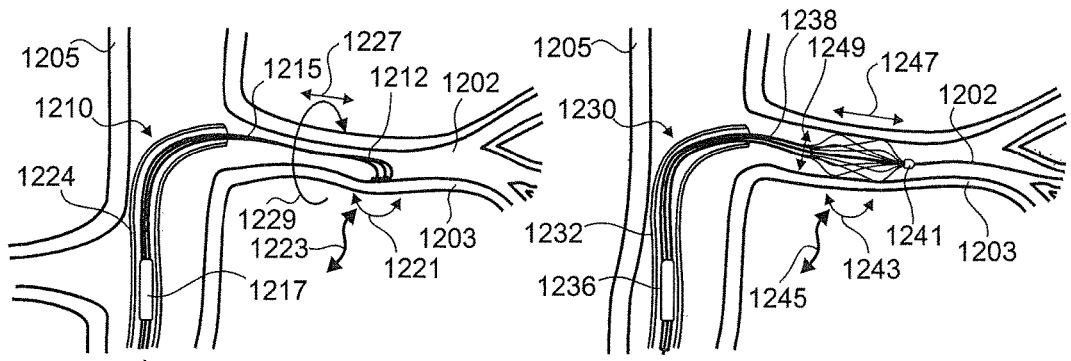
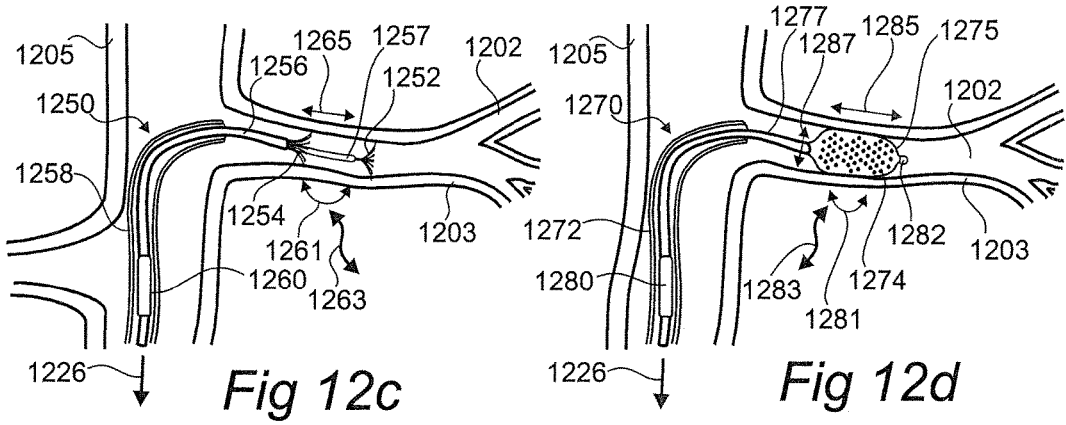
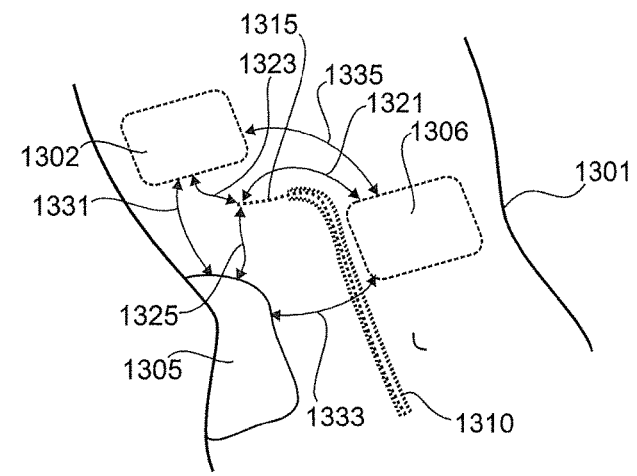

CONTROLLED SYMPATHECTOMY AND MICRO-ABLATION SYSTEMS AND METHODS

CROSS-REFERENCE TO RELATED APPLICATION

The present application is a national stage application of International Application No. PCT/US2013/023157 which claims benefit of and priority to U.S. Provisional Application Ser. No. 61/590,812 filed on Jan. 26, 2012, entitled "Controlled Sympathectomy and Micro-Ablation Systems and Methods", by Landy Toth et al., and U.S. Provisional Application Ser. No. 61/613,097 filed on Mar. 20, 2012, entitled "Controlled Sympathectomy and Micro-Ablation Systems and Methods", by Landy Toth et al., the entire contents of which are incorporated by reference herein for all purposes.

BACKGROUND

Technical Field

The present disclosure relates to the field of minimally invasive sympathectomy. The disclosure relates to methods for locating, monitoring, and/or mapping nerve distributions before, during, and/or following an ablation process facilitated by way of catheterization procedures. The disclosure relates to systems and methods for monitoring the extent of an ablation process as it pertains to a surgical goal, such as denervation. The disclosure also relates to catheter systems specifically designed for use in vascular nerve monitoring and ablation.

Background

Congestive heart failure, hypertension, diabetes, and chronic renal failure have many different initial causes; however, all may include some form of renal sympathetic nerve hyperactivity. Renal sympathetic nerves communicate signals with sympathetic centers located in the spinal cord and brain via afferent renal nerve activity, increasing systemic sympathetic tone; meanwhile, through efferent activity, renal nerves and arteries participate in sympathetic hyperactivity in response to signals from the brain, further increasing systemic sympathetic tone.

Sympathetic activation can initially be beneficial but eventually becomes maladaptive. In a state of sympathetic hyperactivity, a number of pathological events take place: abnormalities of hormonal secretion such as increased catecholamine, renin and angiotensin II levels, increased blood pressure due to peripheral vascular constriction and/or water and sodium retention, renal failure due to impaired glomerular filtration and nephron loss, cardiac dysfunction and heart failure due to left ventricular hypertrophy and myocyte loss, stroke, and even diabetes. Therefore, modulation (reduction/removal) of this increased sympathetic activity can slow or prevent the progression of these diseases.

Although ablation of such nerves can have positive effects on drug resistant hypertension and glucose metabolism abnormality current methodologies for denervation (e.g. ablation) are conducted without adequate feedback (with respect to the site of a denervation event, the extent of denervation, the effect of denervation on local physiology, etc.).

SUMMARY

One objective of this disclosure is to provide a microsurgical tool for monitoring, evaluating, mapping, and/or modulating electrophysiological activity in the vicinity of a lumen within a body. Another objective is to provide a system and method for evaluating the sympathetic tone of a subject. Yet another objective is to provide a system for neuromodulating an anatomical site in the vicinity of a lumen within a body.

The above objectives are wholly or partially met by devices, systems, and methods according to the appended claims in accordance with the present disclosure. Features and aspects are set forth in the appended claims, in the following description, and in the annexed drawings in accordance with the present disclosure.

According to a first aspect there is provided, a microsurgical tool for monitoring electrophysiological activity within the vicinity of a lumen, the microsurgical tool including a microfinger in accordance with the present disclosure having a substantially elongate structure configured so as to bias a region thereof against a wall of the lumen upon deployment within the lumen, and a sensing tip in accordance with the present disclosure electrically and mechanically coupled to the microfinger in the vicinity of the region, configured to interface with the wall of the lumen, the sensing tip configured to convey one or more electrophysiological signals associated with the activity.

In aspects, one or more of the electrophysiological signals may be related to one or more of water concentration, tone, evoked potential, remote stimulation of nervous activity, an electromyographic signal [EMG], a mechanomyographic signal [MMG], a local field potential, an electroacoustic event, vasodilation, vessel wall stiffness, muscle sympathetic nerve activity (MSNA), central sympathetic drive (e.g. bursts per minute, bursts per heartbeat, etc.), tissue tone, nerve traffic (e.g. post ganglionic nerve traffic in the peroneal nerve, celiac ganglion, superior mesenteric ganglion, aorticorenal ganglion, renal ganglion, and/or related nervous system structures), combinations thereof, or the like.

In aspects, one or more of the sensing tips may include one or more electrodes, a needle electrode, a force sensor, mechanomyographic (MMG) sensing element, a strain sensor, a compliance sensor, a temperature sensor, combinations thereof, or the like each in accordance with the present disclosure. In aspects, one or more sensing tips may be electrically coupled with a microcircuit, the microcircuit configured to condition the signal.

In aspects, the microcircuit may be embedded into the microsurgical tool and at least a portion of the electrical coupling may be provided via the microfinger. In aspects, the microcircuit may be embedded into the sensing tip or the microfinger.

In aspects, one or more of the microfingers may be configured so as to substantially embed the sensing tip into the wall of the lumen, to substantially maintain contact with the wall of the lumen while it is swept longitudinally down the lumen and/or circumferentially around the lumen, to substantially maintain a constant force against the wall of the lumen during relative movement there between, to substantially electrically isolate the sensing tip from a cavity of the lumen, to plunge the electrode (particularly a needle electrode) into the wall of the lumen upon deployment, combinations thereof, and the like.

In aspects, the microfinger may include an active material element in accordance with the present disclosure, configured to alter the contact force between the region or the sensing tip, and the wall upon receipt of a control signal.

In aspects, the microfinger may be configured so as to be deployed from a delivery catheter. In aspects, the delivery catheter may have a diameter less than 3 mm, less than 2 mm, less than 1 mm. In aspects, at least a portion of the delivery catheter may have a diameter of less than 0.75 mm, less than 0.5 mm, less than 0.25 mm so as to access a miniature lumen within a body.

In aspects, the microfinger may have a characteristic width of less than 150 um, less than 100 um, less than 75 um, less than 50 um, less than 25 um, less than 10 um, less than 5 um.

In aspects, the microsurgical tool may include a plurality of microfingers, each microfinger configured so as to substantially independently bias against the wall of the lumen upon deployment.

In aspects, a plurality of microfingers may be configured to form a cage, a mesh, or a stent-like structure, to independently maintain contact with the wall during relative movement there between, combinations thereof, or the like.

In aspects, one or more sensing tips may be configured to convey signals in the presence of the relative movement. In aspects, one or more of the sensing tips may include a needle electrode, the associated microfinger configured to plunge the needle electrode into the wall of the lumen upon deployment.

In aspects, one or more of the sensing tips may include a mechanomyographic (MMG) sensing element configured to generate a mechanomyographic signal (MMG) from the activity, and/or a compliance sensor, configured to generate a tissue tone signal.

According to aspects there is provided use of a microsurgical tool in accordance with the present disclosure to monitor electrophysiological activity in the vicinity of a vessel, an artery, a vein, a renal artery, similar structures, or the like.

According to aspects there is provided use of a microsurgical tool in accordance with the present disclosure to perform a surgical procedure.

According to aspects there is provided, a system for neuromodulating an anatomical site in the vicinity of a lumen, including a subsystem configured to perform a surgical procedure on the anatomical site, a microsurgical tool in accordance with the present disclosure, configured to monitor electrophysiological activity in the vicinity of the site; and a control unit configured to accept signals from the microsurgical tool, and to adjust the surgical procedure dependent upon the signals, to display the signals, to evaluate the surgical procedure dependent upon the signals, to plan a surgical path dependent upon the signal, to determine the extent of the procedure dependent upon the signals, combinations thereof, or the like.

In aspects, the surgical procedure may include an ablation, an excision, a cut, a burn, a radio frequency ablation, radiosurgery, an ultrasonic ablation, an abrasion, a biopsy, delivery of a substance, combinations thereof, or the like.

In aspects, the system may include a stimulation and/or ablation electrode configured so as to convey a pulsatile and/or radio frequency signal to the anatomical site from the control unit, the microsurgical tool configured to convey one or more feedback signals related to the pulsatile and/or radio frequency signals back to the control unit. In aspects, the feedback signals may be related to an electrode impedance, a bioimpedance, a local electrical field, or an electrophysiological response to the pulsatile and/or radio frequency signal.

In aspects, the stimulation and/or ablation electrode may be included within the microsurgical tool, coupled to a microfinger, included in a sensing tip, or the like.

In aspects, the control unit may be configured to sweep one or more of the sensing tips along the lumen wall, to use one or more of the electrophysiological signals to locate the anatomical site, to use one or more of the electrophysiological signals to exclude the anatomical site from a surgical procedure, combinations thereof, or the like.

According to aspects there is provided, a method for determining an afferent electrophysiological activity and an efferent physiological activity in the vicinity of a lumen, including monitoring electrophysiological activity at a plurality of sites within the vicinity of the lumen in regions proximal and distal to a target region as measured along a length of the lumen, applying energy to a site within the target region to form a neurological block thereby, and extracting an afferent signal from activity in the distal region and an efferent signal from activity in the proximal region.

In aspects, the method may include comparing activity measured in the proximal region and the distal region to determine if the energy application affected the electrophysiological activity in the vicinity of the target region. In aspects, the method may include evaluating the coherence between activities measured in the proximal region and the distal region and/or using the coherence to evaluate the extent of the neural block.

In aspects, the application of energy may be sufficient to form a temporary neuroblock (i.e. just sufficient to form a temporary block, controlled so as to form a temporary block, etc.). In aspects, the method may include comparing activities from the proximal region and the distal region during the temporary neuroblock and diagnosing a neurological condition, evaluating a neurological state, determining if a permanent surgical procedure is required, combinations thereof, or the like.

According to aspects there is provided, a method for evaluating sympathetic tone of a subject, including inserting a microsurgical tool in accordance with the present disclosure into a lumen of the subject, recording the electrophysiological signals conveyed by the microsurgical tool from a wall of the lumen, removing the microsurgical tool from the lumen, and generating a metric relating to sympathetic tone from the recorded signals.

In aspects, the method may include monitoring another physiological parameter remotely from the lumen to generate a corrective signal and using the corrective signal to remove movement artifacts from the electrophysiological signals.

In aspects, the method may include stimulating one or more anatomical sites in the subject during the recording, and/or diagnosing a medical condition based at least in part upon the metric.

According to aspects there is provided. a method for monitoring and/or evaluating electrophysiological activity in the vicinity of a lumen, including biasing an electrode against a wall of the lumen; and recording one or more electrophysiological signals from the activity in the vicinity of the electrode.

In aspects, the method may include recording one or more of an evoked potential, remote stimulation of nervous activity, an electromyographic signal [EMG], a mechanomyographic signal [MMG], a local field potential, an electroacoustic event, vasodilation, vessel wall stiffness, muscle sympathetic nerve activity (MSNA), central sympathetic drive (e.g. bursts per minute, bursts per heartbeat, etc.), tissue tone, nerve traffic (e.g. post ganglionic nerve traffic in the peroneal nerve, celiac ganglion, superior mesenteric ganglion, aorticorenal ganglion, renal ganglion, and/or related nervous system structures) in the vicinity of the lumen.

The method may include electrically isolating the electrode from a cavity of the lumen, embedding the electrode into the wall of the lumen, sweeping the electrode along the wall of the lumen, generating a map of electrophysiological activity from the recordings obtained during the sweep, recording electrophysiological activity from a plurality of electrodes, cancelling one or more movement artifacts from the recordings, combinations thereof, or the like.

In aspects, the method may include biasing a mechanomyographic (MMG) sensing element against the wall of the lumen and recording a mechanomyographic signal (MMG) from the activity.

According to aspects there is provided, a method for performing controlled neuromodulation in the vicinity of a lumen, including monitoring electrophysiological activity at one or more sites within the vicinity of the lumen to obtain a first activity level, applying energy to a treatment site within the vicinity of the lumen, monitoring electrophysiological activity at one or more sites within the vicinity of the lumen to obtain a second activity level, and comparing the first activity level and the second activity level to determine if the energy application affected the electrophysiological activity, if sufficient energy was applied, if further energy should be applied, combinations thereof, and the like.

In aspects, the electrophysiological activity may relate to one or more of an evoked potential, remote stimulation of nervous activity, an electromyographic signal [EMG], a mechanomyographic signal [MMG], a local field potential, an electroacoustic event, vasodilation, vessel wall stiffness, muscle sympathetic nerve activity (MSNA), central sympathetic drive (e.g. bursts per minute, bursts per heartbeat, etc.), tissue tone, nerve traffic (e.g. post ganglionic nerve traffic in the peroneal nerve, celiac ganglion, superior mesenteric ganglion, aorticorenal ganglion, renal ganglion, and/or related nervous system structures) as measured in the vicinity of the lumen.

In aspects, the method may include determining if sufficient energy has been applied to the treatment site based on the comparison, evaluating the first activity level to determine a suitable treatment site in the vicinity of the lumen, mapping electrophysiological activity in the vicinity of the lumen using the first activity level, applying a stimulus in the vicinity of the lumen, recording electrophysiological activity before, during, and/or after the stimulus, or the like.

In aspects, the method may include recording electrophysiological activity in a proximal region and a distal region measured along the length of the lumen as spaced with respect to the treatment site, to determine if the energy application affected the electrophysiological activity in the vicinity of the treatment site, determining if the energy application was sufficient to form a neural block using the comparison, applying sufficient energy to the treatment site to form a temporary block and assessing if the change in electrophysiological activity is desirable, if so, applying sufficient energy to the treatment site so as to form a substantially irreversible block, or the like.

In aspects, the energy may be provided in the form of a radio frequency current, an ultrasonic wave, thermal energy, a neuroblocking agent, radiation, electromagnetic radiation, radiosurgically generated radiation, combinations thereof, or the like.

In aspects, one or more of the steps of a method in accordance with the present disclosure may be performed using a surgical tool in accordance with the present disclosure.

According to aspects there is provided a method for determining a state of a neurological connection along a neurological pathway between one or more regions in a body, including applying a pacing signal to a lumen in the vicinity of the neurological pathway, monitoring one or more of water concentration, tone, blood oxygen saturation of local tissues, evoked potential, stimulation/sensing of nervous activity, electromyography, temperature, blood pressure, vasodilation, vessel wall stiffness, muscle sympathetic nerve activity (MSNA), central sympathetic drive (e.g. bursts per minute, bursts per heartbeat, etc.), tissue tone, blood flow (e.g. through an artery, through a renal artery), a blood flow differential signal (e.g. a significantly abnormal and or sudden change in blood flow within a structure of the body, a vessel, an organ, etc.), blood perfusion (e.g. to an organ, an eye, etc.), a blood analyte level (e.g. a hormone concentration, norepinephrine, catecholamine, renin, angiotensin II, an ion concentration, a water level, an oxygen level, etc.), nerve traffic (e.g. post ganglionic nerve traffic in the peroneal nerve, celiac ganglion, superior mesenteric ganglion, aorticorenal ganglion, renal ganglion, and/or related nervous system structures), or combinations thereof, or the like at one or more sites within the body to generate one or more physiological signals; and evaluating the influence of the pacing signal on the physiological signals and determining the state of neurological connection therefrom.

In aspects, the method may include applying energy in the vicinity of the lumen so as to induce a neurological block along the neurological pathway, pacing and monitoring before and after induction of the neurological block, and/or comparing the physiological signals obtained before the neurological block to those obtained during the neurological block to determine the influence of the neurological block there upon, combinations thereof, and the like.

In aspects, the method may include determining if the neurological block is favorable in terms of treating an underlying disease state in the body, and/or applying energy in the vicinity of the lumen so as to induce a substantially permanent neurological block along the neurological pathway.

In aspects, the method may include monitoring electrophysiological activity at a plurality of sites within the vicinity of the lumen in regions proximal and distal to the pacing site and/or to the site of a suspected or known neurological block.

In aspects, the method may include extracting an afferent signal from activity in the distal region and an efferent signal from activity in the proximal region and/or comparing activity measured in the proximal region and the distal region to determine if the energy application affected the electrophysiological activity in the vicinity of the target region.

According to aspects there is provided, use of a method in accordance with the present disclosure for evaluation of the effectiveness of a neuromodulation procedure within a body.

BRIEF DESCRIPTION OF THE DRAWINGS

Several aspects of the disclosure can be better understood with reference to the following drawings. In the drawings, like reference numerals designate corresponding parts throughout the several views.

FIGS. 4a-b show aspects of interactions between multiple micro-tips and a lumen wall in accordance with the present disclosure.

FIGS. 5a-c show aspects of micro-tips in accordance with the present disclosure.

FIGS. 6a-b show aspects of a microfinger in accordance with the present disclosure.

FIGS. 11a-g show aspects of non-limiting examples of ablation patterns applied to a lumen wall (i.e. an artery, a renal artery, etc.) in accordance with the present disclosure.

FIGS. 12a-d show aspects of micro surgical tools in accordance with the present disclosure deployed at a surgical site.

FIG. 13 shows a schematic diagram of interaction between one or more macroelectrodes and a micro surgical tool deployed at a surgical site in accordance with the present disclosure.

DETAILED DESCRIPTION

Figure 1A:
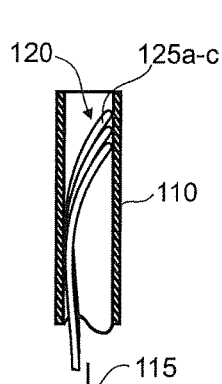
FIGS. 1a-c show aspects of a surgical tool tip in accordance with the present disclosure in a delivery mode and a deployed mode.

Particular embodiments of the present disclosure are described hereinbelow with reference to the accompanying drawings; however, the disclosed embodiments are merely examples of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

A controlled nerve ablation system may include the capability to sense one or more physiological parameters at one or more points around a surgical site, and/or include the capability to stimulate and/or ablate tissues at one or more of the same points and/or an alternative point around a surgical site. In aspects, the nerve ablation system may be configured so as to access a lumen, a vessel, very narrow vessels, and/or surgical sites in the body. The non-limiting examples disclosed herein are directed towards such configurations (e.g. so as to controllably ablate renal nerves along a renal artery with a catheterized procedure).

By lumen is meant a substantially hollow structure, with one or more walls, enclosing a cavity. In the context of the present disclosure, a lumen is generally considered elongate in shape, having a longitudinal direction running along the length thereof, a radial direction running substantially perpendicularly to a wall of the lumen, and a circumferential direction running substantially perpendicular to the longitudinal direction along a wall of the lumen. In aspects, a lumen may include a branch (a bifurication), a bend, a tortuous pathway, a changing diameter (i.e. a diameter that changes along the length thereof), and the like. It is envisaged that a system in accordance with the present disclosure may be apt at navigating such complicated features, thus providing therapy to a range of challenging to reach locations.

The nerve ablation system may include one or more sensing tips (e.g. as located on a micro-tip, a wire, an electrode in a matrix, on a flexible balloon, etc.). One or more sensing tips may include a pressure sensor, a tonal sensor, a temperature sensor, an electrode (e.g. to interact with a local tissue site, provide a stimulus thereto, measure a potential therefrom, monitor current to/from the tissues, to measure a bioimpedance, measure an evoked potential, an electromyographic signal [EMG], an electrocardiographic signal [ECG], a mechanomyographic signal [MMG], a local field potential, etc.), an acoustic sensor, an oxygen saturation sensor, or the like.

The sensing tips may be configured to elucidate a range of key physiological aspects before, during, and/or after a procedure. The following description outlines some non-limiting approaches in this respect. Such sensing tips may be integrated into one or more microfingers, micro-tips, flexible circuits, stretchable substrates, etc.

In aspects, one or more sensing tips in accordance with the present disclosure may be configured to monitor bioimpedance between one or more sensing tips to determine the degree of contact between the finger tips and the anatomical site, and/or potentially the bias force between the finger tips and the anatomical site. Additionally, alternatively, or in combination, bioimpedance measurements between one or more sensing tips may be useful in determining when adequate contact has been made as well as how much current should be applied to an anatomical site during an ablation procedure. Furthermore, additionally, alternatively, or in combination bioimpedance between one or more sensing tips may be used to determine the status of tissue positioned there between. In one non-limiting example, the bioimpedance spectrum between two or more sensing tips may be used to map the local tissue impedance. Such information may be useful to elucidate where such tissue has been completely ablated, where tissue has yet to be ablated, etc.

In aspects, bioimpedance measurement between on or more sensing tips, a sensing tip and a separate electrode, etc. may be used to determine a state of isolation between one or more of the sensing tips and a local fluid (i.e. to determine a state of isolation between a sensing tip and fluid within a lumen, between a sensing tip and blood, etc.).

In aspects, one or more sensing tips in accordance with the present disclosure may be configured to obtain mechanomyographic information during a procedure as determined by slight changes in an associated strain measurement, tip vibration, and/or contact force measurement (e.g. via direct force measurement between the tip and the local anatomy, and/or via changes in the deformation of the microfinger as measured by an associated micro strain gage attached thereupon). Mechanomyographic information may be related to local nervous activity either naturally occurring or in response to a stimulus (e.g. optionally applied by one or more sensory tips, locally, remotely, during and/or via a local RF pulse, etc.). In aspects, a sensing tip may include a piezoresistive strain gauge, a piezoelectric microtransducer, an interfacial pressure sensing membrane or the like to detect mechanomyographic signals. In one non-limiting example, the sensing tip may be coated with a micro or nano coating of a piezoresistive and or piezoelectric material (e.g. a piezoelectric polymer, an electret, a nano-particulate filled elastomer, a conjugated polymer, etc.). In aspects, the mechanomyographic tip may be configured so as to measure one or more aspect of the tissue compliance of the local tissues (e.g. so as to identify calcified material, cancerous tissues, etc.).

In aspects, one or more sensing tips in accordance with the present disclosure may be configured to monitor an electrophysiological signal. Such electrophysiological monitoring at and/or between one or more sensing tips, may be used to map nervous response, electromyographic response (EMG), evoked potential, local field potential, extracellular field potentials, etc. along and/or within the wall of the local anatomical site (e.g. the wall of a lumen, a vessel wall, an artery wall, a venous wall, an organ wall, etc.). Such information may be advantageous for selecting tissues on which to perform a surgical procedure (e.g. an ablation procedure, a biopsy, etc.), to follow and/or map a nerve along the length of the surgical site (e.g. along the wall of an artery, a vein, a tubule, etc.), to determine the state of a surgical procedure, etc. In aspects, one or more sensing tips may be configured to monitor a local electromyographic (EMG) signal before, during and/or after a surgical procedure as a means for monitoring local nervous activity. In such aspects, the EMG signals may be used as feedback for monitoring the extent of a denervation procedure.

In aspects, one or more sensing tips in accordance with the present disclosure may be configured to monitor the tone of a tissue within a body. Monitoring the tone (e.g. mechanical properties, wall stiffness, elastic spectral response, mechanical impedance, physiological properties, etc.) of the adjacent tissues may be determined by combining strain and/or force measurement of the sensing tips while applying movement (optionally cyclical or oscillatory movement) to one or more sensor tips. Such sensing tips may be excited locally (e.g. such as by a local piezoelectric transducer, a capacitive transducer, an electrochemical transducer, a smart material, etc.) or globally (e.g. such as by oscillatory torsional oscillations, axial oscillations, linear oscillations of the surgical tool tip, the associated guide wire, catheter, etc.).

In aspects, one or more of the sensing tips may be interfaced asymmetrically with the associated tissues (i.e. with a bent tip, a micro finger, a wire-like finger configured substantially parallel to the tissue surface, oriented at an acute angle thereto, etc.). By asymmetrically is meant such that the sensing tip approaches the associated tissue surface at an angle other than perpendicular thereto. To describe the use of such a tip to monitor local tissue tone and/or for providing a controlled interfacial force before, during and/or after a procedure, for purposes of discussion, a clockwise torsion may be used to advance the sensing tip along the surface of the local tissues and a relatively small counterclockwise torsion may be used to measure the tone of adjacent tissues. By relatively small is meant an excitation that is sufficiently small in amplitude such that the sensing tip may not appreciably slide along the tissue surface. In aspects, one or more sensory tips, in a structure attached thereto, and/or a system in accordance with the present disclosure may include a vibratory exciter may be configured to generate the excitation.

In aspects, such a tone monitor may be combined with interfacial contact sensing, electrophysiological measurement, and/or sensor tip strain measurement in order to generate a wealth of local tissue information before, during, and/or after a surgical procedure. In one non-limiting example, the local tissues may stiffen during an ablation procedure. By monitoring local tissue tone, a stiffness level may be used to characterize when a suitable degree of ablation has been applied so as to irreversibly damage the tissues. Monitoring of a local tissue tone, perhaps at a monitoring site significantly removed from the surgical site such that the surgical procedure does not directly affect tissues in the vicinity of the monitoring site (i.e. does not directly cut, heat, ablate, abrade, the tissues, etc.) may also be advantageous for determining an effect of the surgical procedure on one or more physiological parameters of a tissue (e.g. a vessel wall stiffness, change in nerve activity, change in blood perfusion, etc.) adjacent to the monitoring site.

In aspects, such tone measurement may be useful in determining the local stiffness of tissues (and/or overall wall stiffness of an adjacent vessel, organ, etc.) in contact with a sensing tip array (e.g. so as to determine the type of tissue adjacent to one or more sensing tips, locate plaque, locate a cancerous tumor, etc.). Tone measurement may further be used to characterize the type of tissue with which the tip is interfacing (e.g. muscle, nervous tissue, fat, plaque, cancerous tissue, etc.). In aspects, such information, possibly in combination with bioimpedance data, electrophysiological monitoring, or the like, may be used to determine how much RF energy to apply locally during an RF ablation procedure.

In one non-limiting example of a method for RF ablating tissue, the local tissue tone may be measured before, during, between individual RF pulses, and/or after a train of RF pulses. As the local tissue tone changes during application of the RF pulses, the tonal changes may be used to determine the extent of the therapy. As the RF ablation process is applied to the adjacent tissues (perhaps via one or more sensing tips), the tonal measurements (as determined by one or more sensing tips, perhaps the same tip through which the RF signal may be applied) may be monitored as the tonal measurements may not be significantly affected by the local RF currents.

In aspects, electrophysiological stimulation and/or sensing from one or more sensing tips in a sensing tip array, or a system in accordance with the present disclosure may be used to interface with, monitor and/or stimulate nervous function within a local anatomical structure (e.g. a lumen wall, a vessel wall, along a nerve, an organ wall, a duct, etc.). Such information may be used to hunt for target tissues (e.g. nerves), select tissues for a surgical procedure, to determine the degree of progression of a surgical procedure (e.g. a degree of ablation during RF surgery, etc.).

In aspects, an array of sensing tips may be configured to apply a directional stimulation and/or multi-site sensing so as to selectively treat/monitor only nerves that are configured to send signals in the preferred direction (e.g. to selectively target primarily efferent nerve bundles, afferent nerve bundles, etc.). Such a configuration may be advantageous for treating a neurological disorder with minimal impact to the surrounding anatomy and physiological function of the associated organs.

In aspects, one or more sensing tips in accordance with the present disclosure may include the capability to apply/receive an RF current to/from the surrounding tissue. The RF current may be provided locally between two of more sensing tips, or alternatively between one or more sensing tips and a macroelectrode placed elsewhere on the body (e.g. on a large skin patch over the surgical site, as selected from multiple patches placed over the body, etc.). In a non-limiting example where current is restricted to being applied between sensing tips, the path for current flow may be well controlled, yet may be highly localized. Alternatively, in an example where RF current is passed between one or more sensing tips and one or more macroelectrodes, the direction of current flow may be more challenging to control, but may be used to access tissues more remote from the sensing tips (i.e. farther into the adjacent tissues, deeper into an organ, farther from a lumen wall, etc.).

In aspects, network impedance measurements between one or more sensing tips and one or more macroelectrodes (e.g. as attached to the body of the patient), may be monitored prior to and/or during application of an RF ablation current. Each sensing tip and/or macroelectrode may include an impedance control circuit that may be adjustable such that the overall current flow through the network formed from all the elements is controlled there through. Such a configuration may be advantageous to more precisely control the local ablation process, thus targeting the local tissues with more accuracy, precision, spatial discrimination, and confidence than less controlled approaches.

In another non-limiting example, a plurality of sensing tips may be engaged with the flow of RF current during an ablation process. In aspects, the local impedance of each microfinger and/or sensing tip may be monitored and/or controlled so as to better optimize the current delivered thereto. Additionally, alternatively, or in combination, the local current flow through each sensing tip may be monitored so as to determine the path of the RF current flow, to ensure no leakage currents are detected, etc. Such information may be used to more precisely control the delivery of RF currents to the local anatomy during an ablation procedure.

Additionally, alternatively, or in combination, before, during and/or after the RF current is applied to the surrounding tissues, one or more sensing tips may monitor a physiological parameter (e.g. water concentration, tone, blood oxygen saturation of local tissues, evoked potential, stimulation/sensing of nervous activity, local field potential, extracellular activity, EMG, temperature, etc.) to determine the extent of completion of the intended surgical procedure.

In aspects, one or more sensing tips may include an optical microsensor (e.g. a micropackage including a light source and/or a CMOS photosensor) and/or a fiber optic element. During a surgical procedure, the optical microsensor may be positioned against or near to the local tissues for analysis before, during and/or after an ablation procedure.

In aspects, an optically configured sensing tip (or group of tips) may be configured to locally assess blood perfusion and/or blood oxygenation in the tissues adjacent thereto. The system may be configured to automatically adjust and/or halt the surgical procedure based upon changes in this signal. Alternatively, additionally, or in combination, the system may alert a user (e.g. a surgeon, an attendant, etc.) to a change in this signal before, during, and/or after a surgical procedure. Such a configuration may be useful for assessing local tissue health before, during, and/or after a surgical procedure, the extent of a surgical procedure, etc.

In another non-limiting example, one or more optically configured sensing tips may be configured so as to be biased towards the tissues of a lumen, a vessel, or the like in the vicinity of the surgical site. The optical sensing tips may include one or more light sources (e.g. light emitting diodes, fiber optic tips, etc.) configured to deliver narrow, multi-band, and/or wideband light to the adjacent tissues. In aspects, one or more of the optical sensing tips may include one or more photodetectors (e.g. a photodetector, a phototransistor, a fiber optic tip, etc.) to receive and/or analyze the light reflected from the adjacent tissues. The received light may be related to that emitted by one or more of the light sources, or may be received from an ambient light source, perhaps located to the exterior of the vessel, or the exterior of the subject's body.

The sources may be configured to emit light at predetermined wavelengths such that different absorption characteristics of the adjacent tissues, perhaps dependent on the wavelengths, may be observed during the surgical procedure. The photodetectors may be configured to receive at least a portion of this light, so as to assess the absorption characteristics with the system (perhaps via a pre-amplification system in accordance with the present disclosure, in an attached electronics unit, etc.). The photodetected signals may be used to determine an oximetry value or a signal related thereto.

In one non-limiting example, the optically configured sensing tips may be biased towards a site on the vessel wall before, during, and/or after the surgical procedure. Alternatively or in combination, the optically configured sensing tips may be substantially stationary with respect to the vessel wall (such as via being attached to a collar of known size, attached to a structure of known width, as part of a structure that is expanded to a known radius, etc.). In aspects, the magnitude of the bias may be controlled by sensors and actuators both accordance with the present disclosure. Changes in the optical signals detected by the photodetectors (perhaps due to changing bias force) before, during and/or after a surgical procedure may be related to changes in the bias force with which they are held against the vessel wall. Such a configuration may be advantageous for determining a change in sympathetic tone and/or vasodilation before, during and/or after a surgical procedure.

In one non-limiting example, the optically configured sensing tips may be coupled with one or more strain and/or interfacial force measurement methods, perhaps to give a more precise reading of the bias force between the sensing tip(s) and the adjacent tissues, to compensate for movement related artifacts, or the like.

In aspects, one or more of the optical sources may be selected such that the penetration of the light into the adjacent tissues may be controlled. In one non-limiting example, a blue wavelength and a red wavelength may be emitted into the tissues. The blue wavelength may provide information relating to the deformation and absorption near to the surface of the tissues, while the red wavelength may penetrate more deeply into the adjacent tissues, providing a signal that changes in response to deformation of tissues farther from the contact site(s) between the tip(s) and the tissue. The photodetectors or equivalent optical detection pathway may include filters, polarized windows, or the like to separately assess the different spectra during an analysis. Comparison between photodetected signals in the blue spectrum with those obtained from the red spectrum may be used to determine tone and/or elastic modulus of the tissues of the vessel in the vicinity of the sensing tip(s). Such a configuration may be advantageous for assessing sympathetic tone (i.e. via muscular tension measurement), and/or vasodilation, vessel wall stiffness, and/or local tissue stiffness before, during and/or after a surgical procedure. Changes in such properties may be indicative of the degree of completion of the surgical procedure.

In aspects, an externally placed (e.g. onto the body of the subject) light source (e.g. infrared, near infrared, visible, etc.) may be directed into the body towards the surgical site. The light source may optionally be modulated to provide a more easily detected signal within the subject. One or more sensing tips equipped with optical microsensors may sense light emitted from the light source. The mapping of received light may be used to locate and/or localize one or more anatomical features such as nerves near to one or more of the optical microsensor equipped sensing tips.

In aspects, one or more externally placed light sources may be used to help locate the anatomical sites of interest during the procedure. An external light source may include a narrow band light source, a broad band light source, light sources spaced apart from each other, and/or combinations thereof. The light sources may be modulated so as to be more easily detectable by sensors located on, in, or near to the anatomy of interest. In one non-limiting example, a plurality of light sources may be aimed at the surgical site from distinct vantage points within the body (i.e. as accessed via an endoscopic procedure, etc.) or externally to the body (i.e. as positioned at locations on the body).

In another non-limiting example an endoscopic camera may be placed near to the anatomy, lumen wall, and/or surgical site during a procedure to observe both the anatomy, as well as placement of the surgical tools in the vicinity of the anatomy. In one non-limiting example, the endoscopic camera and/or light source may provide a suitable macro-electrode for RF ablation processes performed during the surgical procedure.

In another non-limiting example, one or more sensing tips may be equipped with a corresponding micro-light source (e.g. an oLED, an LED, etc.). The micro-light source may be used to direct light into the adjacent tissues. One or more sensing tips equipped with optical microsensors may be configured to detect light emitted from the micro-light source as back scattered by the adjacent tissues. Such information may be used to detect anatomical features (e.g. nerves, tumors, etc.) in the adjacent tissues.

Such optical configurations may be advantageous for mapping the local tissues before, during and/or after a surgical procedure. They may also be advantageous for implementation into a nerve detection system (e.g. perhaps as input to a nerve hunting algorithm, etc.).

In one non-limiting example, the system may include a micro balloon catheter for placement into a vessel (e.g. a renal artery, etc.). The micro balloon catheter may be coated with a thin layer of an indicator molecule. The indicator molecule may be tagged to attach to the target tissue of interest and/or tagged so as to change chromatic properties when bound to the target tissue (e.g. nervous tissue, etc.). The molecules may be delivered to the desired tissues during a balloon catheterization procedure. During such a procedure, the micro balloon catheter may be placed into the vessel of interest and inflated so as to kiss the walls of the vessel. While in contact with the vessel walls, the indicator molecules may attach and migrate/diffuse into the local tissues. Such a procedure may be performed as a first surgical step or as combined with other aspects in accordance with the present disclosure. In aspects, the balloon may also be configured to deliver a therapeutic agent (i.e. a neuroblocking agent, ethyl alcohol, botox, etc.) to the anatomy of interest.

In a method in accordance with the present disclosure, one or more sensing tips are inserted into a lumen with a wall within a body and biased towards the wall of the lumen, and one or more electrophysiological signals obtained therefrom. The electrophysiological signals may be analyzed to locate one or more target tissues for a surgical procedure (i.e. one or more sympathetic nerves, parasympathetic nerves, etc.). A bolus of therapeutic agent, an RF current, a thermal energy source, and/or the like may be delivered to the identified tissues so as to perform the surgical procedure thereupon. In aspects, one or more post-procedural electrophysiological signals may be analyzed to determine the extent of the surgical procedure.

In aspects, the therapeutic agent may be provided via a micro balloon catheter in accordance with the present disclosure. In aspects, the therapeutic agent may be delivered via one or more microfingers in accordance with the present disclosure.

In aspects, the micro balloon catheter may include one or more sensory tips (e.g. in the form of functional elements attached to the balloon, attached to a superstructure surrounding the balloon, etc.) in accordance with the present disclosure.

In aspects, the bioimpedance and/or electrophysiological signals between one or more sensing tips in the array and one or more sensing tips in the array, an external electrode, a reference electrode, or the like may be used to determine changes in the structure of the adjacent tissues during an ablation procedure. Such information may be useful in determining the extent of the ablation procedure, char accumulation, etc.

In aspects, bioimpedance measurements may be correlated with nerve damage data, perhaps obtained during prior surgeries, development of the procedure, and/or obtained during specific testing procedures, such that changes in local bioimpedance data may be used during a surgical procedure to determine the extent of the ablation procedure. Such a configuration may be advantageous in the case that the surgical procedure itself overwhelms the local electrophysiological activity to the extent that neurological monitoring may be hindered for a prolonged period of time after the procedure has been completed.

In aspects, one or more sensing tips may be configured to monitor local electrical fields during an ablation procedure in accordance with the present disclosure in order to better determine the current flow path through the adjacent anatomy, perhaps connected to a warning system to indicate to an operator when the ablation field is insufficient for achieving the intended goal. Such a configuration may be advantageous for avoiding unnecessary damage to the tissues during a misfired or misdirected ablation session.

In aspects, a system in accordance with the present disclosure may include a micro balloon catheter including one or more sensory tips (e.g. in the form of functional elements attached to the balloon, attached to a superstructure surrounding the balloon, etc.). The micro balloon catheter may be configured so as to bias the sensory tips against the adjacent vessel walls, thus providing a reliable interface from which selective ablation and detection processes may be performed. Such a micro balloon catheter may be advantageous for single placement type surgical procedures in accordance with the present disclosure.

In aspects including a plurality of sensing tips (e.g. as placed onto a micro balloon catheter, a microfinger array, a microtool set, a flexible cage assembly, etc.) the sensing tips may be interconnected with each other, with signal processing circuitry, a local control circuit, and the like and/or combinations thereof. In order to substantially reduce the number of signal wires that must be sent to the surgical site during the procedure, the networked array of sensing tips may be multiplexed together with a locally placed control circuit (e.g. an application specific integrated circuit, distributed/interconnected circuit elements, a collection of flexible semiconducting circuit elements, etc.). The control circuit may be configured to communicate such signals with an extracorporeal system (e.g. a computer, a control system, an RF ablation controller, a data acquisition system, etc.). The control circuit may be configured to communicate with the extracorporeal system via analog and/or digital means and/or methods. In one non-limiting example, the communication may be of primarily digital means such that the control circuit may exchange data pertaining to any sensing tip in the array, as well as switch data, control data, RF pulse routing, etc.

In another non-limiting example, the networked array of sensing tips may be interconnected with distributed electronic elements and flexible electrical interconnects (e.g. as applied to a balloon wall, as provided by structural wires, microfingers, wire mesh elements, etc.). In aspects, one or more of the sensing tips, microfingers, or the like may be included upon a flexible or stretchable electronic substrate, the electronic substrate configured to interface the sensing tips with the anatomy as well as to electrically connect one or more sensing tips, or the like with a controller, a control system, an operator, a graphical user interface, a display, or the like.

A controlled nerve ablation system in accordance with the present disclosure may include one or more microfingers.

To this effect, a microfinger array microsurgical tool is disclosed herein. Any element in the microfinger array may include a sensing tip in accordance with the present disclosure to interact with the local anatomy during a surgical procedure.

The microfinger array may be advantageous for accessing very small anatomical sites within a body, perhaps through tortuous vessels, deep into an organ, etc.

A microfinger array may be arranged in a surgical tool in accordance with the present disclosure such that one or more of the microfingers may substantially independently interface with the adjacent tissues. Thus if an array of microfingers is placed against a rough or otherwise uncontrolled surface, each microfinger may be able to contact, maintain a controlled bias force against, substantially embed an associated sensing tip into, and/or substantially maintain contact with the surface during use, even if the microfinger array is dragged along the surface as part of a procedure, during movement of the surface, etc. Such independently adjustable microfingers may be advantageous so as to maintain a known interfacial pressure, especially while monitoring, stimulating and/or ablating the tissue with the microfingers. Such independently adjustable microfingers may be advantageous to substantially embed an associated tip (i.e. an associated sensory tip) into an adjacent tissue during a procedure.

By microfinger is meant a substantially curved finger like member (i.e. with curvature at one or more points along the length thereof, with multi-axial curvature, etc.). Such microfingers may generally have a characteristic width (although may be of any cross sectional makeup). The microfingers may generally have characteristic widths on the order of approximately 1 mm, 0.5 mm, 0.1 mm, 0.05 mm, 0.01 mm, or the like. In one non-limiting example, one or more microfingers may include a Nitinol structure (e.g. a wire, a ribbon, etc.) with characteristic width of approximately 50 um.

In aspects, one or more regions of a microfinger in accordance with the present disclosure may be selectively coated with an isolation layer (e.g. an oxide layer, a dielectric coating, a polymer layer, a lubricious layer, etc.). In aspects, such an isolation layer may be selectively applied to regions of the microfingers (i.e. so as to create isolated regions and sensitive regions thereof).

In aspects, the microfingers may be configured so as to deploy and/or bias against one or more adjacent tissues during a procedure and may be used to contact ably sweep the local anatomy, for purposes of sensing and/or ablating during a surgical procedure. In aspects, one or more microfinger dimensions and structure may be designed so as to provide substantially uniform and predictable bias forces on the adjacent tissues over a wide range of movements and dimensional variation.

In aspects, an array of microfingers in accordance with the present disclosure may be configured so as to sufficiently collapse down into a delivery catheter while expanding radially outwards upon deployment so as to form a controllably biased contact within a tubular anatomical structure (e.g. an artery, a vein, an intestinal wall, etc.).

In aspects, one or more microfingers in accordance with the present disclosure may be configured into the shape of a wire basket, a mesh-like structure, or the like. In aspects, one or more regions of such microfingers may be patterned with an isolation layer, so as to direct signals over the microfingers, towards associated sensing tips, to provide communication between associated sensing tips and control electronics, to control one or more mechanical properties thereof, or the like.

Such a configuration may be advantageous for accessing tight anatomical spaces of interest (e.g. small vessel walls), while also maintaining consistent contact forces at a surgical site during a procedure, substantially embedding one or more sensory tips into a lumen wall, substantially isolating one or more sensing tips from an adjacent fluid, or the like.

In aspects, a microfinger array in accordance with the present disclosure may include a plurality of fingers, one or more such fingers configured to interface with the surrounding tissues and biased radially outwards from a deployment site (e.g. a guide wire, a catheter, etc.). In aspects, the microfinger array may be deployed via longitudinal retraction of a restraining shell (i.e. a restraining layer in the catheter), via application of heat or current (i.e. in the case of a shape memory microfinger, etc.), via projection of the microfinger array out of a delivery catheter (i.e. by advancing the microfinger array beyond the tip of the delivery catheter, etc.).

In aspects, one or more microfingers may include a spring-like wire element (e.g. Nitinol, spring steel, etc.) and/or may include composite structures including a spring-like element to provide a bias force so as to push the tip and/or one or more regions of the microfinger towards the wall of a vessel into which it is placed (i.e. towards a surface, a lumen wall, a vessel wall, etc.).

In aspects, a microfinger may include a Nitinol structure, optionally configured for passage of current flow, to and from the surrounding tissues, and/or communication of electrophysiological information between an associated sensing tip and a connected microcircuit. In aspects, the Nitinol structure may be configured such that, when an RF pulse is applied there through towards the surrounding tissues, the Nitinol structure may retreat from the tissues after a predetermined amount of energy has passed there through, upon reaching a predetermined temperature, or the like. Thus the Nitinol structure may provide an inherently controlled method for applying a quantum of RF energy to the surrounding tissues. Such a configuration may be adapted for use simultaneously, additionally, alternatively and/or in combination with one or more of the other aspects described in this disclosure.

In aspects, each finger in the array may move somewhat independently of the others such that all fingers may maintain contact with the vessel wall during a procedure.

Such a configuration may be advantageous for maintaining robust contact with the walls of a tortuous anatomical site (e.g. a plaque filled artery, a tortuous vein, a damaged vessel, etc.) within the body. Such a configuration may be advantageous for maintaining robust contact with the walls of a lumen, surgical site, etc. while performing a procedure (i.e. scanning a surface with one or more microfingers, dragging a microfinger along a surface, monitoring a tissue site, ablating a tissue site, etc.) or during periods of relative movement (i.e. in the presence of organ movement, perhaps due to physiological processes, stresses related to biorhythms, breathing, blood pressure, etc.).

In aspects, at least a portion of the microfingers may be formed as spirals such that torsion applied at the operator end of the catheter may rotate the microfingers about the central axis of the lumen (i.e. blood vessel, etc.), thus allowing one to sweep the contact of the microfingers around the entirety of the vessel interior. Such movements may be advantageous for analyzing the adjacent tissues, selectively mapping and ablating the tissues, etc. In one non-limiting example, a microfinger array in accordance with the present disclosure may be swept circumferentially along the wall of a vessel, optionally starting and stopping so as to analyze the local tissues. If a suitable site for ablation is detected, the microfinger array may be used to ablate the tissues as well as monitor the ablation process to ensure controlled ablation is achieved before continuing with the sweeping procedure.

In aspects, the microfingers may be formed slightly off axis, such that relative axial movement of an overlying sheath may be used to retract the microfingers into the sheath or conversely to deploy them towards the anatomical site. Additionally, alternatively, or in combination, off axis arrangements may provide the capability to sweep the microfingers circumferentially along the anatomical site via applying torsion to the guide wire, delivery wire, and/or catheter to which they are attached.

Such a configuration may be advantageous for simultaneously mapping and selectively ablating an anatomical site during a surgical procedure.

Furthermore, such a configuration may be advantageous for working upon an anatomical site, while maintaining flow of fluid there through (i.e. as opposed to an occlusive tool, which may block flow during expansion thereof).

In aspects, one or more microfingers may be provided with highly miniaturized and flexible structure so as to more easily access highly restricted anatomical sites within the body.

In aspects, one or more microfingers may include one or more sensing tips in accordance with the present disclosure for capturing information from the local surgical site. Some non-limiting examples of sensing options include temperature sensors, electrodes, strain gauges, contact force sensors, combinations thereof, and the like. For purposes of discussion, a sensing tip may also be referred to as a microsensor.

The sensing tips may be configured to elucidate a range of key information during a procedure. Some non-limiting examples are discussed in more detail below.

Bioimpedance between one or more microfinger tips may be used to determine the degree of contact between the finger tips and the anatomical site, as well as potentially the bias force between the finger tips and the anatomical site. Such information may be useful in determining when adequate contact and to gauge how much current should be applied to an anatomical site during an ablation procedure.

Mechanomyographic information may be obtained from fingertips during a procedure as determined by slight changes in an associated strain measurement and/or contact force measurement (e.g. via direct force measurement between the tip and the local anatomy, and/or via changes in the deformation of the microfinger as measured by an associated micro strain gage attached thereupon).

Evoked potential monitoring at or between one or more finger tips, may be used to map nervous response, electromyographic response, extracellular potentials, local field potentials, evoked potential, etc. along the wall of the local anatomy (e.g. vessel wall, organ wall, etc.). Such information may be advantageous for selecting tissues on which to perform a surgical procedure (e.g. an ablation procedure, a biopsy, a stimulation procedure, etc.).

The tone of the adjacent tissues may be determined by combining strain and/or force measurement of the microfingers while applying an excitation to one or more microfingers (e.g. optionally clockwise torsion to advance the microfingers and small counterclockwise torsion to measure the tone of adjacent tissues, a vibratory exciter in combination with contact and/or microfinger strain measurement, etc.).

Such tone measurement may be useful in determining the local stiffness of tissues in contact with the microfinger array (e.g. so as to determine the type of tissue adjacent to one or more microfingers, to locate plaque, to locate a cancerous tumor, etc.).

Stimulation and sensing from one or more microfingers in the microfinger array may be used to elicit nervous function of local anatomy. Such information may be used to select tissues for a surgical procedure, to determine the degree of progression of a surgical procedure (e.g. a degree of ablation during RF surgery, etc.). Directional stimulation and sensing may be used to selectively treat only nerves that are configured to send signals in the preferred direction (i.e. via combination of stimulation and/or sensing from a plurality of sensing tips, sensing sites, etc.).

In aspects, one or more microfingers may include the capability to apply/receive an RF current to/from the surrounding tissue.

Such RF currents may be applied between one microfinger in the array and an (optionally) distant counter electrode, between two or more microfingers in the array, to a extracorporeal patch on the body, etc.

In aspects pertaining to multiple microfinger RF current passage, the local impedance of each microfinger may be altered so as to control the current delivered thereto.

In aspects pertaining to multiple microfinger RF current passage, the local current flow through each microfinger may be monitored so as to determine the path of the RF current flow, to ensure no leakage currents are detected, etc. Such information may be used to more precisely control the delivery of RF currents to the local anatomy during an ablation procedure.

In aspects, prior to, during, and/or after the RF current is applied to the surrounding tissues, one or more microfingers may be configured to monitor a physiological parameter (e.g. water concentration, tone, blood oxygen saturation of local tissues, evoked potential, stimulation/sensing of nervous activity, emg, temperature, etc.) to determine the extent of completion of the intended surgical procedure.

In aspects, the bioimpedance between one or more microfingers in the array may be used to determine changes in the structure of the adjacent tissues during an ablation procedure. Such information may be useful in determining the extent of the ablation procedure, char accumulation, etc.

In aspects, bioimpedance measurements may be correlated with nerve damage data, perhaps obtained during prior surgeries or obtained during specific testing procedures, such that changes in local bioimpedance data may be used during a surgical procedure to determine the extent of the procedure. Such a configuration may be advantageous in the case that the surgical procedure itself overwhelms the local electrophysiological activity to the extent that neurological monitoring may be hindered for a prolonged period of time after the procedure has been completed.

In aspects, one or more microfingers may be configured to monitor local electrical fields during an ablation procedure in order to better determine the current flow path through the adjacent anatomy, perhaps connected to a warning system to indicate to an operator when the ablation field is insufficient for achieving the intended goal, to assist with the direction of energy towards the intended surgical site, to conserve energy, etc. Such a configuration may be advantageous for avoiding unnecessary damage to the tissues during a misfired ablation session.

A system may include an embolic net to capture char that may form during the ablation procedure. Such netting may be advantageous for preventing surgically related emboli from traveling throughout the body after the surgery.

In aspects, the system and/or microfingers may include a coolant delivery system (e.g. a saline delivery system) in order to cool the microfingers during and/or after an ablation procedure. Such coolant delivery may be advantageous for minimizing char and excessive damage associated with an ablation procedure. Such coolant delivery may be part of a cryogenic surgical procedure, or the like.

In aspects, the system may include multiple microfinger arrays, perhaps located at specific radii from each other such that when sweeping a tubular anatomical site (e.g. a vessel), the bias forces may be reasonably maintained between the microfingers and the tissue walls.

In aspects, one or more microfingers may include an exposed electrode area (i.e. as part of an electrode based sensing tip) that only touches the walls of the adjacent anatomy. Such a configuration may be advantageous for minimizing current flow into the adjacent fluids within the vessel, to better control RF current flow in the vicinity of the electrodes, minimize conductivity between the exposed area and the surrounding fluid, so as to substantially embed the exposed electrode area in to the wall of the adjacent anatomy, etc.

In aspects, one or more microfingers may include one or more active material elements. Control signals delivered to the active material element may help to bias the microfingers towards the intended surgical site, actively control the contact forces between finger tips and the surgical sites, etc. Some non-limiting examples of active materials that may be suitable for application to one or more microfingers include shape memory materials (e.g. shape memory alloys, polymers, combination thereof), electroactive polymers (e.g. conjugated polymers, dielectric elastomers, piezoelectric polymers, electrets, liquid crystals, graft elastomers, etc.), piezoceramics (e.g. amorphous piezoceramics, single crystals, composites, etc.). In addition the active material may be used as a vibratory exciter and/or mechanical probe, for use in monitoring the tone of the adjacent tissues (see above), alternatively, in addition or in combination, to cause vibratory/ultrasonic ablation and/or local heating to the tissues. In such aspects, the active material may be included along the length and/or over a region of the microfinger (i.e. so as to influence the shape of the microfinger during contraction or expansion of the active material).

In aspects, one or more microfingers may include an electrical shield such that the microfinger tips are effectively shielded from other currents flowing through an associated catheter, the body, etc. during a procedure.

In aspects, one or more elements of a microfinger based catheter may include a bidirection switching network, micro amplifier array, a sensory front end, combinations thereof, or the like in order to amplify sensed signals as close as possible to the anatomical interface, to switch the function of a microfinger tip between sensory, stimulatory, and/or ablative functions, perform combinations thereof, or the like. In aspects, the circuitry may be included in the delivery wire within the catheter of the system. In such aspects, the circuitry may be coupled to one or more microfingers and/or sensing tips each in accordance with the present disclosure, and a secondary signal acquisition circuit, a digital communication block, a controller, an RF signal generator, combinations thereof, and the like.

In aspects, a bidirectional switching network may be used to enable bifunctional stimulation/sense capabilities in one or more microfingers, etc. The switching network may be included in a local amplifier array, as a flexible circuit, or silicon die interconnected to or placed upon one or more microfingers, etc. Alternatively, additionally, or in combination, an extracorporeal circuit element may be coupled to the switching network and/or microfingers, sensing tips, etc. and to a controller included within a surgical system including a microfinger array in accordance with the present disclosure.

In aspects, a micro amplifier array may be used to preamplify the signals obtained from one or more sensory aspects of the microfingers, so as to improve the noise signature, etc. during use. The microamplifier may be coupled to the catheter, embedded into the catheter, embedded into one or more microfingers, etc.

In aspects, one or more microfingers in accordance with the present disclosure may be provided such that they are sufficiently flexible so as to buckle, or change orientation during back travel, so as to prevent puncture of the local anatomy. A configuration as outlined in this non-limiting example may be advantageous for providing contact with the local anatomy without significant risk of damaging the adjacent anatomy (e.g. puncturing a vessel wall, etc) which may be a concern with stiffer, more traditional structures. Such microfingers may include a characteristic width of less than 200 um, less than 100 um, less than 50 um, less than 25 um, less than 10 um.

In aspects, one or more microfingers in accordance with the present disclosure may include a substantially hyper elastic material (e.g. formed from a memory alloy material, a superelastic material, a spring steel, etc.) so as to effectively deploy from a very small deployment tube/catheter and expand outward to accommodate a large range of vessel diameters. Such a configuration may be advantageous in so far as a small number of unit sizes may be suitable for treating a wide range of anatomical structures. In addition, the designed curvature and form of a microfinger may be substantially chosen so as to further enable a wide deployable range of movement.

A surgical tool including a plurality of microfinger arrays (i.e. clusters of microfingers, fans of microfingers, etc.) may be employed so as to determine physiological response more remotely from an intended surgical site than may be available within a single array. Aspects of the disclosed concepts may be employed along the same lines by extending interactions between microfingers within an array, to inter-array interactions. In aspects, a surgical tool including a plurality of clustered microfinger arrays may be advantageous to analyze one or more anatomical sites simultaneously from a plurality of sites (macroscopically separated sites). In one non-limiting example, two microfinger arrays may be arranged along a catheter based surgical tool, so as to interface with the walls of a lumen, at two or more longitudinally separated distances. Physiological sensing from multiple microfingers may be advantageous for determining the extent of neurological traffic between the plurality of sites, determine the direction of traffic, determine if traffic from one direction or the other is blocked (i.e. after a surgical procedure, after RF current application, after a denervation procedure, etc.). Such configurations and methods for determining the state of a plurality of anatomical sites is further disclosed throughout the text and appended figures of this disclosure.

In aspects, a system in accordance with the present disclosure may be used to monitor physiological activity associated with a surgical site prior to, during and/or after a surgical procedure is applied thereto. Some suitable examples of surgical procedures include an RF ablation, Argon plasma coagulation, laser ablation, ultrasonic ablation, cryoablation, microwave ablation, abrasion, biopsy, delivery of a substance (e.g. a chemical, a drug substance, an acid, a base, etc.), combinations thereof, and the like. The local physiological activity (e.g. nervous activity, blood perfusion, tonal changes, muscular sympathetic nerve activity, etc.) may be monitored with one more sensors (sensing tips, microfingers, etc.) and/or associated stimulators each in accordance with the present disclosure. Additionally, alternatively, or in combination, a technique for assessing one or more physiological properties and/or states of an associated surgical site may be employed. Such techniques include assessing values and/or trends in bioimpedance, blood pressure, tissue oxygenation, tissue carbon dioxide levels, local temperatures and changes thereof, and the like.

In aspects, the system may include a substrate onto which the sensing tips may be placed. Such a substrate may be formed from a balloon wall, a mesh, an interwoven ribbon array, a cloth, etc. The substrate may include stretchable and/or flexible electronic materials.

Electrical interconnects may be formed from carbon nanotubes (e.g. SWNTs, MWNTs, etc.), nanowires, metallic wires, composites, conductive inks, and the like.

In aspects, a portion, or all of the substrate and/or an associated substrate carrier film may be formed from polyurethane, a silicone, a general elastomer, silk fibroin materials, or the like and/or combinations thereof. Inclusion of microporous or fibrous substrates, may be advantageous to allow the substrate or substrate carrier film to adhere to the adjacent tissues via capillary effects (i.e. tendencies to wick fluid from adjacent tissues into the substrate). The thickness of films formed from the material may be less than 30 um thick, less than 20 um, less than 10 um, less than 4 um, less than 1 um. Composites of somewhat stiffer materials (such as polyimide, PET, PEN, etc.) and somewhat softer materials (e.g. silicones, polyurethanes, thermoplastic elastomers, etc.) maybe used to compromise between overall structural stiffness and conformal capabilities of the substrate.

In aspects, patterned overcoats and/or composite layers may also be used to expose electrode materials and/or sensing tips to the surrounding tissues in the vicinity of measurement regions, etc.

In one non-limiting example, the substrate may be at least partially formed from a silk material (e.g. Bombyx mori cocoons). The material may be processed to remove sericin (which may cause undesirable immunological response) using methods known in the art. The resulting material can be solvent cast into shapes and crystallized to form self-supporting structures.

In aspects, adaptive temperature estimation may be used to better control the RF process. Such techniques may be supported by use of a surgical tool in accordance with the present disclosure, including one or more sensing tips configured with temperature and/or bioimpedance monitoring aspects. Modeling of changes in local bioimpedance may be related to local temperature changes during the ablation process. Such measurements as well as local thermoconductive properties, tissue thermoconduction, etc. may also influence the rates at which a local ablation process may take place (i.e. as related to a thermal ablation process).

In aspects, a system in accordance with the present disclosure may include one or more microsensors for monitoring nervous activity and/or related physiological activity during the RF ablation process. Some examples of suitable monitoring techniques include electromyography (EMG), muscle sympathetic nerve activity (MSNA), mechanomyography (MMG), phonomyography (PMG), extracellular potentials, local field potentials, combinations thereof, and the like. Mechanomyography (MMG) measures the force created by local muscle contractions caused by associated neural activity. Phonomyography (PMG) measures low frequency sounds associated with movement generated by associated neural activity. Traditionally, techniques such as MMG and PMG have been employed on externally accessible nervous and muscular tissues. One advantage of such techniques is that they may not be as easily affected by local electrical noise as EMG and the effects of the nervous activity may be generally sensed farther from the associated nerve than with electromyographic techniques.

Alternatively, additionally or in combination the ascribed sensing techniques may be combined with stimulation from local sources in accordance with the present disclosure. Such stimulation and sensing may be advantageous in determining functionality of local nerves without the need to listen to complex biologically generated nervous activity. Furthermore, combined stimulation and sensing may be advantageous for determining functionality of a local nerve in real-time during a denervation and/or ablation procedure (e.g. the successive stimulation and sensing may be used to determine the degree of neurological block and/or neuromuscular block there between). In aspects, such functionality as well as directionality of the nerve signal propagation (e.g. efferent, afferent, etc.) may be more easily determined through use of combined local stimulation and sensing.

In aspects, one or more patterns of nerve stimulation may be used to determine the function of the local nerve structures as well as one or more aspects of neurological block and/or neuromuscular block that may be caused by the surgical procedure (e.g. ablation), anesthesia, heating, chemical delivery, a related condition, etc.

In aspects, a single stimulation may be applied to elicit maximal response from the associated nerve at frequencies of less than 10 Hz, less than 1 Hz, less than 0.1 Hz. The downstream response as measured by any of the described techniques will depend on the frequency with which the stimuli are applied. In aspects, in order to allow for complete recovery of the nerve between stimulations, a frequency of less than or equal to 0.1 Hz may be advantageous.

During RF ablation of an associated nervous structure, the evoked electrical and/or muscular responses may be dramatically affected. Such changes in the response may be useful in determining the state of the denervation procedure. Thus they may be advantageous to determine the exact degree of RF energy that must be applied to a given structure in order to cause sufficient denervation as desired by a surgical procedure. Such an approach may be advantageous to limit damage to surrounding tissues caused by the denervation procedure, to ensure suitable denervation has been achieved, to determine which nerves are affected by the procedure, to control the extent of a denervation procedure, etc.

Another technique for stimulation and sensing of the nervous response includes applying a rapid succession of pulses followed by a period of inactivity. Pulse trains may be used to gradually force a nerve into a blocked state. The rate at which a nerve enters a blocked state and later recovers therefrom may be a suitable indicator of the overall health and functionality of the nerve (i.e. a suitable metric for determining how a procedure has affected that nerve).

In aspects, the sensing of the nervous response may not need to be local to a surgical site, but rather downstream (in the sense of the flow of an associated nervous signal) from the site. Such sensing of the nervous response may be advantageous for determining the progression of a particular form of communication past a surgical site (i.e. afferent, efferent traffic, etc.).

In aspects, various mapping techniques may be applied to the surgical site, before, optionally during and after a surgical procedure. Some mapping techniques as used in cardiac interventions include pace mapping, activation mapping, entrainment mapping, and substrate mapping. It may be feasible to adapt such techniques for use in the intended application. In general, these techniques may complement each other in localizing where amongst a surgical site to target the ablation procedure.

In one non-limiting example, the micro fingers and/or associated sensing tips may be arranged in a polar configuration as an array of arches (i.e. an array of thin, arch-like elements each extending radially outwards from a central axis). The arches may be attached at each end, a first end connected to an axially oriented draw wire and the other end attached to a collar. The arches may be collapsed and/or expanded radially by extending and/or retracting the length of the draw wire between the first end and the collar respectively. The draw wire may extend through the surgical tool to the operator or a machine, where force on the draw wire may be used to achieve this function. Thus the arches may be provided in a substantially collapsed state (i.e. with small overall diameter) for easy delivery to the surgical site. Upon delivery to the surgical site, the draw wire may be retracted, perhaps automatically and/or with the help of an operator and the arches may be extended radially outwards, so as to contact the adjacent tissues of the vessel. Such a procedure may be used to bias the array of sensing tips and/or micro fingers towards the walls of the vessel while maintaining blood flow there through.

Alternatively, additionally, or in combination the arches may be deployed at a surgical site by removal of a restraining sheath (perhaps by retraction), by dissolution of a restraining element (e.g. an adhesive, an electrochemically destructible member, etc.), via thermal self-expansion of one or more elements of the arches, by combinations thereof, or the like.

Additionally, or in combination to the aspects described herein, the surgical system may be configured to monitor one or more physiological parameters at one or more locations in the body remote from the surgical site. Some non-limiting examples of what may be monitored include water concentration, tone, blood oxygen saturation of local tissues, evoked potential, stimulation/sensing of nervous activity, electromyography, temperature, blood pressure, vasodilation, vessel wall stiffness, muscle sympathetic nerve activity (MSNA), central sympathetic drive (e.g. bursts per minute, bursts per heartbeat, etc.), tissue tone, blood flow (e.g. through an artery, through a renal artery), a blood flow differential signal (e.g. a significantly abnormal and or sudden change in blood flow within a structure of the body, a vessel, an organ, etc.), blood perfusion (e.g. to an organ, an eye, etc.), a blood analyte level (e.g. a hormone concentration, norepinephrine, catecholamine, renin, angiotensin II, an ion concentration, a water level, an oxygen level, etc.), nerve traffic (e.g. post ganglionic nerve traffic in the peroneal nerve, celiac ganglion, superior mesenteric ganglion, aorticorenal ganglion, renal ganglion, and/or related nervous system structures), combination thereof, and the like.

In aspects, a surgical system in accordance with the present disclosure may include one or more elements to monitor physiological activity and/or analyte levels (e.g. a hormone level), in and/or near to one or more portions of a gland, an endocrine gland (e.g. an adrenal gland, an adrenal medulla, etc.), etc.

In another non-limiting example, a multi catheter surgical system may be employed, each catheter in accordance with the present disclosure. In this non-limiting example, one or more first catheters may be used to probe and/or ablate tissues at a first surgical site (e.g. an artery, a renal artery, a left renal artery, etc.) while one or more second catheters may be configured to monitor one or more physiological parameters elsewhere in the body (e.g. in an alternative artery, a vein, in an organ, at a lymph node, at a ganglion, etc.), perhaps to determine the effect of the surgical procedure there upon. In one non-limiting example, the catheters may be inserted into the same or closely positioned entry points into the body (e.g. the femoral artery, iliac artery, radial artery, femoral vein, etc.). Such a configuration may be advantageous for providing a minimally invasive surgical tool to perform the surgical procedure (e.g. a sympathectomy, a renal sympathectomy, etc.).

Figure 1B:
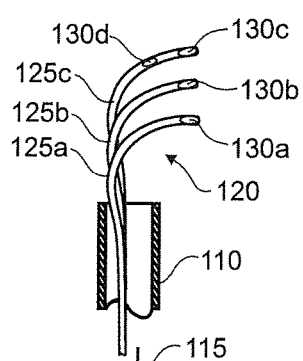
Figure 1C:
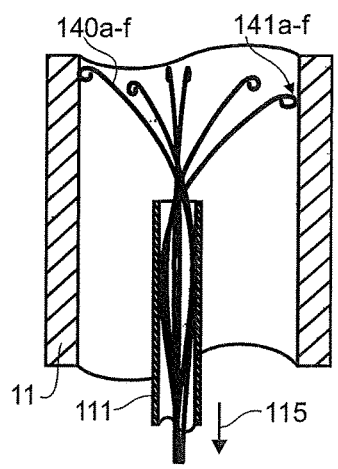

FIGS. 1a-c show a surgical tool tip in accordance with the present disclosure in a delivery mode and a deployed mode.

FIG. 1a shows a delivery catheter 110 with a micro surgical tool 120 held within (e.g. in a retracted position). The micro surgical tool 120 may include one or more microfingers 125 in accordance with the present disclosure for use in a surgical procedure (e.g. a denervation procedure, a biopsy, an excision procedure, etc.). The micro surgical tool 120 may be configured so as to reversibly collapse down into the delivery catheter 110 upon retraction. The microsurgical tool 120 and/or delivery catheter 110 may be connected 115 to a controller, a control unit (e.g. with a deployment control switch, etc.), an operator, a signal conditioning circuit, etc.

FIG. 1b shows a deployed micro surgical tool 120 with a plurality of microfingers 125a-c (i.e. in this case, 3 microfingers are shown). In aspects, the microsurgical tool 120 may include any reasonable number of microfingers 125a-c. Each microfinger 125a-c may be generally spaced apart from the others such that if the array is biased towards a tissue site, they may form a pattern (e.g. a dotted line, a diamond, a ring, etc.). The microfingers 125a-c may be expand outward (e.g. radially, axially, circumferentially, and/or combinations thereof) in one or more directions when deployed from the associated delivery catheter 120. Thus the microfingers 125a-c may suitably engage with a local tissue site be it to monitor the site, ablate the site, a combination thereof, or the like. One or more of the microfingers 125a-c may include one or more sensing tips 130a-d each in accordance with the present disclosure. As shown in this non-limiting example, each microfinger 125a-c includes a sensing tip 130a-c located, primarily at the end of the microfinger 125a-c. In addition, one microfinger 125c includes another sensing tip 130d (e.g. perhaps a temperature sensor, a reference electrode, a flow sensor, etc.) located near to the end of the microfinger 125c. In aspects, a temperature sensor 130d in the flow may be advantageous to evaluate local flow changes (turbulence, micro heating, etc.) that may occur during an associated surgical process.

FIG. 1c shows a deployed microtool 135 from a delivery catheter 111, after being placed within a lumen within a body (i.e. a vessel, an artery, a vein, a tubule, etc.). The microtool 135 includes a plurality of microfingers 140a-f each arranged radially around the axis of the lumen and biased against the wall of the lumen 11. In this non-limiting example, the microfingers 140a-f are shown with electrode based sensing tips 141a-f. The microfingers 140a-f are also shown with curled tips, configured so as to minimize stresses applied to the lumen wall 11 during deployment. The electrode based sensing tips 141a-f may include one or more exposed electrically conducting regions (i.e. a metallic material, a conducting polymer, a conjugated polymer, a carbon material, combinations thereof, or the like) so as to interface electrically with the adjacent lumen wall 11. In aspects, the microfingers 140a-f may be coated with an insulating layer in accordance with the present disclosure, so as to minimize fluid contact there along during a monitoring, stimulation, and/or ablation process applied therewith.

Figure 2A:
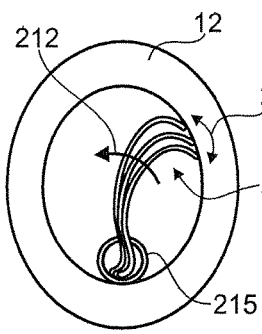
FIGS. 2a-c show aspects of deployed surgical tips in accordance with the present disclosure interacting with a local surgical site.
Figure 2B:
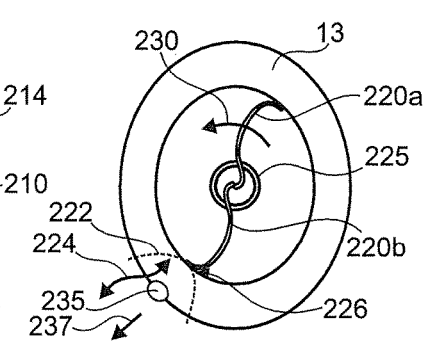

FIGS. 2a-b show deployed surgical microtools in accordance with the present disclosure interacting with a local surgical site. FIG. 2a shows a cross section of a vessel located at a surgical site. The vessel includes a vessel wall 12, which may have one or more anatomical features that are to be operated upon (i.e. nerves, tumor, plaque, etc.). An array of microfingers 210 in accordance with the present disclosure is shown interacting with the vessel wall 12. For purposes of discussion, an associated delivery catheter 215 is also shown in within the vessel wall 12. In the example shown, the microfinger array 210 may be swept along the vessel wall by counter clockwise rotation 212 about the delivery catheter 215 (or clockwise, depending on the preference of the operator, design of the catheter, etc.). Such motion may be provided by an operator (e.g. by torsion of the micro surgical tool shaft), by a mechanism within the tool, by a flexural structure of the microfinger array 210 (e.g. a helical structure so as to prefer rotational sweeping of the anatomy as the array is pulled through the vessel), combinations thereof or the like. The microfingers of the array 210 may include one or more sensing tips each in accordance with the present disclosure configured to interact with the lumen wall 12. In one aspect, shown, one or more of the sensing tips may be configured to pass a current 214 locally between one or more of the sensing tips. Such current may be used to stimulate the local anatomy (i.e. as part of a stimulation/response monitoring system), or at higher intensities, as an RF source for ablation of local tissues (i.e. to perform a localized sympathectomy, etc.). In aspects, the microfinger array 210 may be configured to provide a combination of sensing and ablation (i.e. to perform a controlled sympathectomy procedure, to vary the degree transmission of local signals, to affect one or more local anatomical sites, one or more receptors, etc.).

FIG. 2b shows a multi-array micro surgical tool including two arrays of microfingers 220a-b simultaneously interacting with substantially opposite sides of the vessel wall 13. One microfinger array 220b is shown ablating a local tissue site, thus forming an ablation zone 222. A hypothetical RF ablation current pathway 224 is shown in the figure for purposes of discussion. The multi-array microsurgical tool may be rotated about the delivery catheter 225, in this example, in a counter clockwise direction 230 with respect to the viewer. The microfingers 220a-b include one or more sensing tips 226, in this case, the sensing tip 226 near the ablation site is configured to deliver current to and/or accept current from the local tissues. In a usage scenario, the sensing tips 226, may be configured to monitor local electrophysiological activity in the lumen wall while the surgical tool is rotated about the delivery catheter 225, when an anatomical site 235 of interest (i.e. a nerve plexus, a high traffic nerve plexus, a tumor, etc.) is detected, the ablation process may be initiated through select microfingers in the arrays 220a-b. Current and/or sensing potentials may be provided between a first and one or more sensing tips 226 in the arrays 220a-b, or between a sensing tip 226 and an external electrode (not explicitly shown), located in a direction 237 away from the lumen wall 13.

Figure 2C:
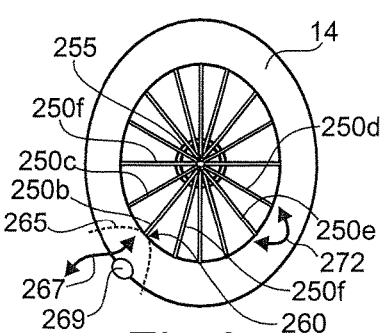

FIG. 2c shows a radially expanding micro surgical tool including an array of microfingers 250a-f (not all elements numbered due to clutter), each microfinger configured to bias against the lumen wall 14 upon deployment from the delivery catheter 255. The microfingers 250a-f may include one or more sensing tips 260 (not all numbered due to clutter) each in accordance with the present disclosure, configured to simultaneously interact with localized regions of the vessel wall 13 upon deployment. A collection of microfingers 250a-c is shown in the process of ablating a local tissue site, thus forming an ablation zone 265. A hypothetical RF ablation current pathway 267 is shown in the figure for purposes of discussion. In a usage scenario, the microfingers 250a-e and associated sensing tips 260 may be configured to bias against the lumen wall 14 and to monitor local electrophysiological activity in the lumen wall while the surgical tool is positioned therein, and/or drawn along the axis of the lumen during a mapping process, etc. In the given example, an anatomical site 269 of interest (i.e. a nerve plexus, a high traffic nerve plexus, a tumor, etc.) is detected near to sensing tip 260, and an ablation process may be initiated through select microfingers in the arrays 250a-c. In aspects, the anatomy of interest may be mapped, and/or the layout of the anatomy determined either via movement of the microtool along the length of the lumen, via coordinated sensing, and/or stimulation/sensing between related microfinger arrays (not explicitly shown), etc. via one or more methods in accordance with the present disclosure. In aspects, two or more of the microfingers 250d-e may be configured to pass current 272 there between, to measure an electrophysiological signal there between, etc. In aspects, the system may include and/or be coupled to a controller, the controller configured to analyze the signals obtained from each microfinger and determine the location and/or state of an anatomical site of interest, determine the extent of an ablation procedure, etc.

Figure 3:
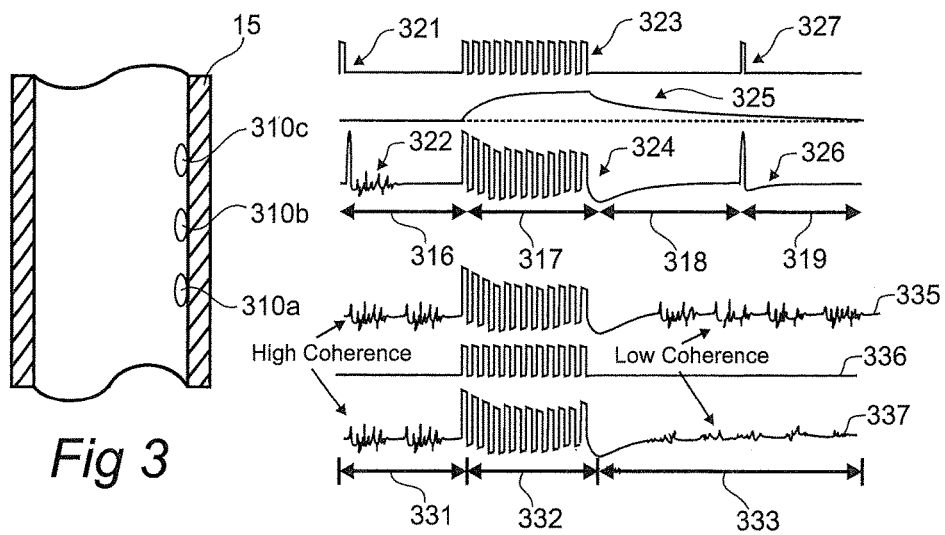
FIG. 3 shows aspects of a plurality of micro-tips configured for monitoring physiological response and/or stimulating local tissue during a surgical procedure in accordance with the present disclosure.

FIG. 3 shows a plurality of micro-tips monitoring physiological response and/or stimulating local tissue during a surgical procedure. Three sensing tips 310a-c are shown abutted against a vessel wall 15. The sensing tips 310a-c may be attached to microfingers, substrates, balloons, or the like (each in accordance with the present disclosure).

In a first example 320, the first sensing tip 310a is used both to stimulate the local tissues (e.g. in order to determine proximity to a local nerve, to determine one or more aspects of local nerve function, etc.), and to ablate the local tissues (e.g. as part of a denervation event, to destroy cancerous tissue, to cauterize a tissue site, etc.). The second sensing tip 310b is configured to monitor local temperature variation of the tissues with which it may be in contact during a surgical procedure. The third sensing tip 310c is configured to sense an electrical response from the local tissues during a surgical procedure (e.g. evoked potential, EMG, microvoltage, current flow, etc.).

FIG. 3 also shows a time series of events for the first example 320, shown during an RF ablation procedure. During a testing period 316 one or more stimulatory pulses 312 may be applied to the first sensing tip 310a and monitored 322 by one or more of the other tips (in this case the third sensing tip 310c). Perhaps during this period the combination of stimulation and response satisfies a predetermined surgical criterion for initiating local ablation (i.e. local nerves identified, overactive neurological traffic detected, etc.). During the ablation period 317, an RF signal 323 is applied to the tissues via the first sensing tip 310a (e.g. perhaps with current flow to the third sensing tip 310c, to a remote macroelectrode, combinations thereof, etc.). The RF ablation may be performed sequentially or with a duty cycle so as to evaluate the progress throughout. It may also be performed in one sequence. The RF signal as measured by the third sensing tip 310c may be used to assist with determining bioimpedance of the local tissues, the state of the local tissues, etc. during the ablation process. In this non-limiting example, local tissue temperature 325 near to the ablation site (as monitored via the second sensing tip 310b) may also be used to estimate the extent of the ablation process, perhaps in combination with sensing via the third sensing tip 310c, and/or bioimpedance measurements. When the temperature and/or ablation process reaches a setpoint, the ablation is stopped and the local tissues are allowed to recover. This timeframe is shown as a recovery period 318. In aspects, the recovery period 318 may be less than 2 min, 1 min, 30 s, 10 s, 1 s, 0.1 s. In an additional testing period 319, the first sensing tip 310a may stimulate the local tissues and the third sensing tip 310c may monitor for a response. In this case, an absent response indicates that the ablation procedure has proceeded sufficiently for the intended purposes and the microsurgical sensory tip array may be advanced to a new site or removed from the lumen.

FIG. 3 also shows a time series of events for a second example 330, shown during an RF ablation procedure. In this example, the first sensing tip 310a and the third sensing tip 310c are configured so as to monitor local electrophysiological response of the tissues (i.e. to monitor extracellular neurological activity, local field potentials, electromyographic signals, etc.) and the second sensing tip 310b is configured to apply an RF current to the lumen wall 15 adjacent there to. During a testing period 331 electrophysiological responses are monitored at the first sensing tip 310a and the third sensing tip 330c. As can be seen from the a-site response curve 335 and the c-site response curve 337, prior to an ablation, the coherence between the sensed signals is high (i.e. closer to 1 than to 0). During the ablation period 332 an RF signal 336 is applied to the tissues via the second sensing tip 310b (e.g. perhaps with current flow to the first sensing tip 310a, the third sensing tip 310c, or to a remote macroelectrode, combinations thereof, etc.). The RF ablation may be performed sequentially or with a duty cycle so as to evaluate the progress throughout. It may also be performed in one sequence. The associated RF signal as measured by the first sensing tip 310a and the third sensing tip 310c may be used to assist with determining bioimpedance of the local tissues, direction of RF current flow from the second sensing tip 310b, the state of the local tissues, etc. during the ablation process. When the temperature and/or ablation process reaches a setpoint, the ablation is stopped and the local tissues are allowed to recover. This timeframe is shown as a recovery period 333. In aspects, the recovery period 333 may be less than 10 min, less than 5 min, less than 2 min, less than 1 min, less than 30 s, less than 10 s, less than 1 s, less than 0.1 s, or the like. During the recovery period electrophysiological responses are monitored at the first sensing tip 310a and the third sensing tip 330c. As can be seen from the a-site response curve 335 and the c-site response curve 337, after the ablation procedure 332, the coherence between the sensed signals has changed dramatically (i.e. it has decreased significantly). The measure of coherence between the signals before and after a surgical procedure, may be a quantifiable indicator of a state of completion thereof, it may be a quantifiable measurement of the local percentage change in neurological activity, it may be an indicator of the ratio of afferent/efferent traffic in the vicinity of the sensing tips 310a-c, and the like. In this case, a markedly changed coherence between the a-site signal 335 and c-site signal 337 indicates that the ablation procedure has proceeded sufficiently for the intended purposes and the microsurgical tool in accordance with the present disclosure, may advance to a new site or removed from the lumen. Such coherence based determination of procedural outcomes may be a suitable method for automatically performing associated surgical procedures, for controlling the extent of such surgical procedures, and the like.

FIGS. 4a-b show interactions between multiple micro-tips and the local vasculature in accordance with the present disclosure. FIG. 4a shows a micro surgical tool in accordance with the present disclosure including three arrays of microfingers 410a-c interacting with the vessel walls 16 of a local anatomical site. The microfinger arrays 410a-c are shown in a deployed state from a delivery catheter 415 in accordance with the present disclosure. In aspects, the microfinger arrays 410a-c may be arranged so as to sufficiently cover the lumen walls 16 after deployment. In aspects, the microfinger arrays 410a-c may be swept along the vessel walls via torsional action of the micro surgical tool or aspect thereof. The microfinger arrays 410*a-c* are shown as swept in a counter clockwise direction 420 in the FIG. 4*a*. A local contact site between a microfinger array 410*c* and the vessel wall 16 is shown in more detail in blowup B. One or more of the microfingers may include one or more sensing tips in accordance with the present disclosure. FIG. 4*b* shows a magnified view of blowup B. Three micro-tips 430*a-b* included in the microfinger array 410*c* are shown pressed against a local tissue site of the lumen wall 16. Each microtip includes a sensing tip 435*a-c* in accordance with the present disclosure. In this case, the sensing tips shown may be electrodes, MMG sensing elements, force sensing elements, temperature sensors, any sensing tip in accordance with the present disclosure, combinations thereof, or the like. A single micro-tip 430*b* is shown with a full outline for further discussion. During a procedure, the micro-tip 430*b* may be swept, oscillated, etc. the tip will interact locally with the tissue (e.g. via transverse movement, changing contact forces, etc.). Such movement may be directed towards/away from the tissue surface (i.e. in a direction normal 445 to the tissue surface), and/or along the surface of the tissue (i.e. in a direction parallel 440 to the tissue surface). Equipped with an associated deflection sensing tip and/or an interfacial pressure sensing tip, these movements may be used to elucidate local physiological properties (e.g. mechanical compliance, tone, etc.) of the tissues. Alternatively, additionally, or in combination a suitably equipped micro-tip 430*b* may be used to measure local mechanomyographic response, perhaps due to electrophysiological activity in the vicinity of, or upstream from the tip 430*b*. Such information may be used for several intended purposes as detailed throughout this disclosure.

In aspects, the microfinger may be equipped with a needle electrode tip (perhaps formed as a structural extension of the flexure, etc.). The needle electrode tip may be configured such that upon applied torsion in a given direction, the needle may pierce the local tissues so as to enhance the electrical interface between the microfinger and the tissues. Such a needle electrode tip may be integrated into one or more microfingers and/or sensing tips in accordance with the present disclosure.

FIGS. 5*a-c* show some non-limiting aspects of micro-tips and/or tips of one or more microfingers in accordance with the present disclosure. FIG. 5*a* shows schematic diagrams for the cross sections of four non-limiting examples of micro-tips in accordance with the present disclosure (i.e. in this case including one or more exposed electrode sensing tips). FIG. 4*a* shows a schematic of the tip of a micro-finger 510 including a core flexure 512 (e.g. a superelastic spring-like material, optionally electrically conducting, a wire, a flex circuit, a micro interconnect, etc.), with an isolating layer 514 (e.g. an oxide, a dielectric coating, a radio-opaque coating, etc.) applied selectively to regions thereof. At the tip of the micro-finger 510, a region 516 of uncoated core flexure is exposed. This region 516 may, provide an electrode property for interacting with local tissues, provide a site for attachment of a microsensor, etc. In aspects, the exposed region 516 may be coated with one or more electrode materials (i.e. one or more metals, alloys, conducting polymers, composites, carbon materials, conjugated polymers, combinations thereof, or the like). In the example shown, the exposed region 516 is oriented to one side of the neutral axis of the core flexure 512. Such orientation may be advantageous for maintaining contact with an adjacent tissue surface while sweeping or moving the micro-tip 510, while biasing the micro-tip 510 against a tissue surface, etc. In aspects, the micro-tip 510 may be configured with a curvature, oriented so as to ensure the exposed region 516 will face an approaching tissue surface during deployment.

FIG. 5*a* shows a schematic of a micro-tip 520 in accordance with the present disclosure. The micro-tip 520 is shown with a core flexure 522 and an insulating layer 524, each in accordance with the present disclosure. The micro-tip 520 may include an axially oriented exposed region 526, located at the tip thereof. The axially oriented exposed region 526 may be configured for electrically interfacing with an adjacent tissue, with a sensing tip (i.e. a sensing tip in accordance with the present disclosure), or the like. Such a configuration may be advantageous for the simplicity of manufacture, etc. The core flexure 522 may be shaped in the vicinity of the exposed region 526 so as to efficiently interface against an adjacent tissue surface.

FIG. 5*a* further shows a schematic of a microfinger 530 in accordance with the present disclosure. The microfinger 530 may include a core-flexure 532 and an insulating layer 534 each in accordance with the present disclosure. The microfinger 530 may include an exposed region 536 in accordance with the present disclosure. The core-flexure 532 may be shaped to a point and/or an edge within the vicinity of the exposed region 536. Such a configuration may be advantageous to cause the microfinger 530 to grip and/or penetrate into a tissue surface when brought into contact therewith.

FIG. 5*a* shows a schematic of a micro-tip 540 in accordance with the present disclosure. The micro-tip includes a plurality of core flexures 542*a-b*, each in accordance with the present disclosure and one or more regions covered with an insulating layer 544 in accordance with the present disclosure. In the example shown, the micro-tip 540 may include a plurality of exposed regions 546*a-b* oriented along the length or near the tip thereof. The exposed regions 546*a-b* may act as electrode based sensing tips in accordance with the present disclosure, may be configured so as to accept one or more sensing tips in accordance with the present disclosure. Such a configuration may advantageous for monitoring local electrophysiological signals, bioimpedance, impedance between the tip region 546*b* and the shank region 546*a* (i.e. so as to determine if the tip is in contact with an adjacent fluid, etc.).

In aspects, the core flexures 542*a-b* may include a flex circuit with a plurality of interconnects. The exposed regions 546*a-b* may include a plurality of contacts for interfacing between the core flexures 542*a-b* and one or more sensing tips attached thereto.

In aspects, one or more of the microfingers 510, 520, 530, 540 may include one or more electrical interconnects arranged along the length thereof, one or more distributed integrated circuit elements, etc.

In aspects, the microtip 510, 520, 530, 540 may include a plated electrode structure, a mushroom like electrode (e.g. so as to increase the contact surface area between the microtip and the tissues), a bent tip, a loop formation, a foot-like electrode element, etc.

In aspects, the microtip 510, 520, 530, 540 may be equipped with a needle electrode tip (perhaps formed as a structural extension of the flexure, etc.). The needle electrode tip may be configured such that upon applied torsion in a given direction, the needle may pierce the local tissues so as to enhance the electrical interface between the microtip and the tissues.

FIG. 5*b* shows a ribbon like microfinger 550 in accordance with the present disclosure. The ribbon microfinger 550 may include a substrate 552 in accordance with the present disclosure, a spring-like material, a flexible polymeric material, or any combination thereof. As shown, the ribbon microfinger 550 includes electrical interconnects 554 coupled to the substrate 552 for communicating one or more electrical signals along the length thereof as well as regions 556*a-b* at the tip suitable for interacting with local tissues (i.e. a site suitable for a sensing tip in accordance with the present disclosure). The electrical interconnects 554 may be coupled to one or more of the regions 556*a-b* (i.e. coupled with one or more electrode based sensing tips, coupled to one or more sensing tip interconnects, etc.).

FIG. 5*c* shows a helical ribbon microfinger 560 in accordance with the present disclosure. The helical ribbon microfinger 560 may include a plurality of sensing tips 566, each coupled to a substrate 562 and optionally to one or more interconnects 566 each in accordance with the present disclosure. The substrate 562 may include one or more embedded microcircuits 568, coupled to the sensing tips 566 and/or the interconnects 566, so as to provide a signal conditioning function, switching function, multiplexing functionality, or the like, in accordance with the present disclosure.

A ribbon microfinger 550, 560 may be configured so as to take on a particular shape (i.e. a hook like shape 559 as shown in FIG. 5*b*, a helical shape 569 as shown in FIG. 5*c*, or the like) upon deployment, perhaps from a delivery catheter in accordance with the present disclosure.

Such a ribbon microfinger 550, 560 may be attachable to a micro balloon catheter, wound around a stent-like mesh, etc. so as to provide support thereto and/or to bias the ribbon microfinger into the adjacent tissues for purposes of monitoring, stimulating, and/or performing a procedure (i.e. heating, ablating, abrading, etc.).

In aspects, the ribbon microfinger 550, 560 may include one or more circuit elements 568 (e.g. a switch, an amplifier, etc.) in order to control direction of, perform a conditioning function to, alter the impedance of, etc. a signal passed along the microfinger (i.e. to or from the micro-tip).

FIGS. 6*a-b* show a microfinger 610 in accordance with the present disclosure. FIG. 6*a* shows an axial view of a microfinger 610 demonstrating an optional multi-axial curvature thereof, as well as a sweeping action 620 that may be achieved therewith during a procedure with the microfinger 610 biased against a lumen wall 17. FIG. 6*b* shows a longitudinal view of the same microfinger 610, demonstrating additional curvature thereof as well as contact between the microfinger 610 and coupled sensing tip 630 with a local anatomical surface (i.e. in this case a vessel wall 17). An arrow 620 is shown in FIGS. 6*a-b* to demonstrate the sense of rotation of the microfinger 610 as it is swept over a vessel wall 17. A lumen axis 18 is also shown so as to demonstrate the approach for the microfinger 610 after deployment from a delivery catheter (not explicitly shown).

Figure 7A:
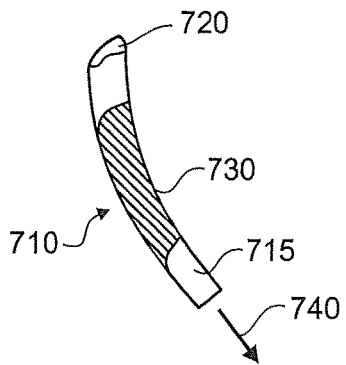
FIGS. 7a-b show aspects of a micro-tip including a mechanomyographic (MMG) sensing element and a typical response in accordance with the present disclosure.
Figure 7B:
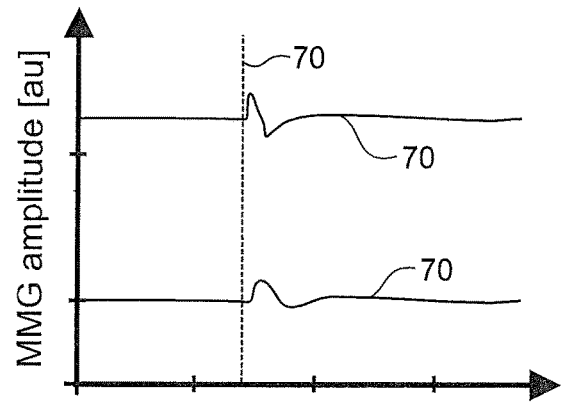

FIGS. 7*a-b* show a micro-tip 710 including a MMG sensing element and a response in accordance with the present disclosure. The micro-tip 710 includes an interfacial force sensing element 720 (e.g. a nanomaterial coating, a piezoresistive coating, a piezoelectric coating, etc.) and a flexural sensing element 730 (e.g. a nanomaterial coating, a piezoresistive coating, a piezoelectric coating, etc.). Both elements 720, 730 may be coupled to the substrate 715 of the microtip 710. The micro-tip 710 maybe subsequently connected 740 to a controller or microcircuit (not explicitly shown) via one or more interconnects, included in the micro-tip (i.e. along a substrate 715 and/or core flexure thereof). Such electrical elements may be embedded into the substrate 715, into a delivery catheter (not explicitly shown), coupled to one or more elements of an associated surgical tool, or the like. The interfacial force sensing element 720 may be configured to measure a contact force between the microfinger 710 and an adjacent tissue surface. The flexural sensing element 730 may be configured to measure flexure of the micro-tip 710 during such interaction. Thus, via monitoring signals from both sensing elements 720, 730 a local compliance of the adjacent tissues may be measured/inferred (i.e. via measurement of contact force, flexure, and/or some combination thereof).

FIG. 7*b* shows a time series of conditioned signals received from a flexural sensor and an associated interfacial force sensor during a stimulation event 750 (e.g. perhaps as excited by another sensing tip included in an associated micro surgical tool, etc.). The stimulation and associated response from each sensor 720, 730 is shown on the time series (i.e. force sensing 760 and strain sensing 770 respectively). In aspects, the stimulation may be caused by an electrical stimulation event, perhaps elsewhere in the body, in a related neurological circuit, or the like. The combination of force sensing 760 and strain sensing 770 signals may be combined to form an MMG signal. The resulting MMG signal(s) may be sufficiently free from electrical noise that may be present when measuring via alternative measures.

Figure 8A:
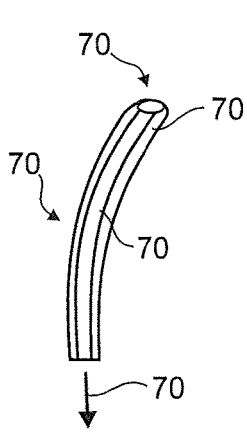
FIGS. 8a-b show aspects of a micro-tip in accordance with the present disclosure.
Figure 8B:
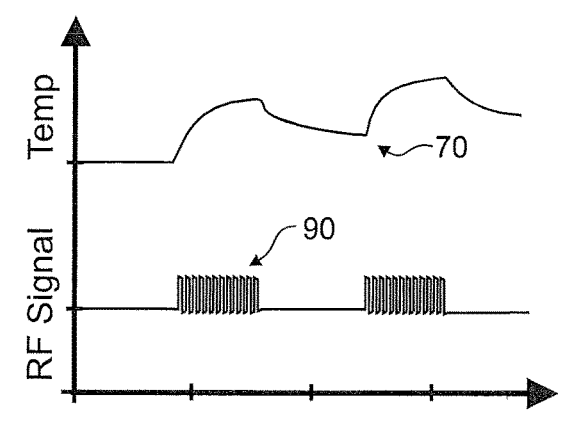

FIGS. 8*a-b* show a schematic of a micro-tip 810 in accordance with the present disclosure. FIG. 8*a* shows a micro-tip 810 with an integrated temperature sensing tip 840. The temperature sensing tip 840 may include a bimetallic configuration, a silicon sensing element, an infrared sensing microcircuit, etc. The micro-tip 810 includes a plurality of electrical interconnects directed between the temperature sensing tip 840 and a controller 850 (e.g. a local control circuit, an analog to digital converter, a local signal amplifier, etc.). The micro-tip 810 may include a substrate and/or core flexure 820 along which such electrical interconnects may be coupled. The micro-tip 810 may include one or more insulating layers 830 in accordance with the present disclosure.

FIG. 8*b* shows a time series measurement from the temperature sensing tip 840 during a series of local RF ablation pulses 860. Local temperature rise 870 as measured by the temperature sensing tip 840 may be used to control the overall pulse width of each RF pulse, the overall RF energy delivery, the RF power, etc. In aspects, such information may be coupled with one or more signals obtained from an associated sensing tip in accordance with the present disclosure. Such information may be collectively used to determine the extent of an ablation process, in deciding to continue with an ablation procedure, or the like.

Figure 9:
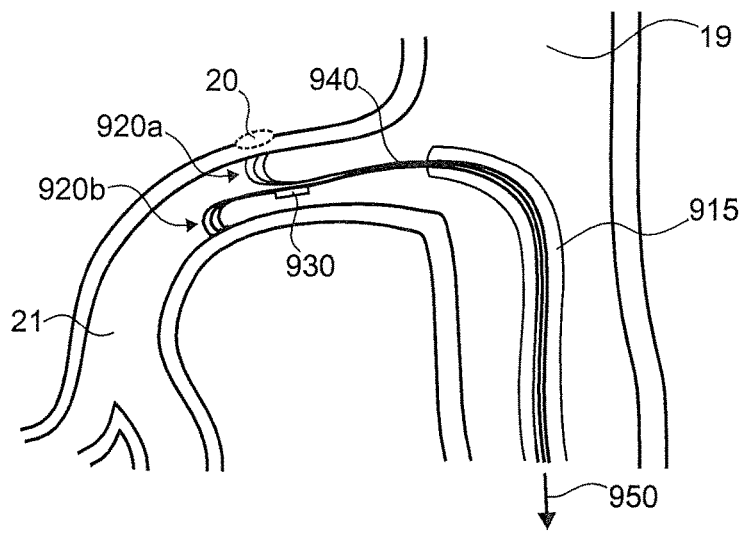
FIG. 9 shows aspects of a micro surgical tool deployed at a surgical site in accordance with the present disclosure.

FIG. 9 shows a micro surgical tool 910 deployed at a surgical site 19, 20, 21 in accordance with the present disclosure. The micro surgical tool 910 includes a delivery catheter 915 and a plurality of microfinger arrays 920*a-b*, the microfinger arrays 920*a-b* penetrating into the renal artery 21 of a subject. The micro surgical tool 910 includes a guide wire 940 (alternatively a guiding arm, a control arm, etc.) coupled to the microfinger arrays 920*a-b* such that they may be controlled by an external operator, robot, etc. (i.e. coupled 950 to the micro surgical tool 910). In the arrangement shown, one of the microfinger arrays 920*b* is attached to a local signal conditioning integrate circuit 930, positioned so as to provide conditioning of signals sensed at the microfinger tips 920*b*, perhaps to convert the signals into digital forms, to provide a low impedance source, etc. The other microfinger array 920*a* is oriented adjacent to an anatomical site 20 of interest (i.e. in this case nerve plexus). The presence/location of the anatomical site 20 of interest may have been determined via monitoring of one or more sensing tips within the microfinger arrays 920*a*-*b* during a sweeping procedure, etc. Having identified/located the anatomical site 20 of interest, the operator, controller, etc. 950 may perform a surgical procedure thereupon.

FIGS. 10*a*-*d* show non-limiting examples of monitoring methods in accordance with the present disclosure.

Figure 10A:
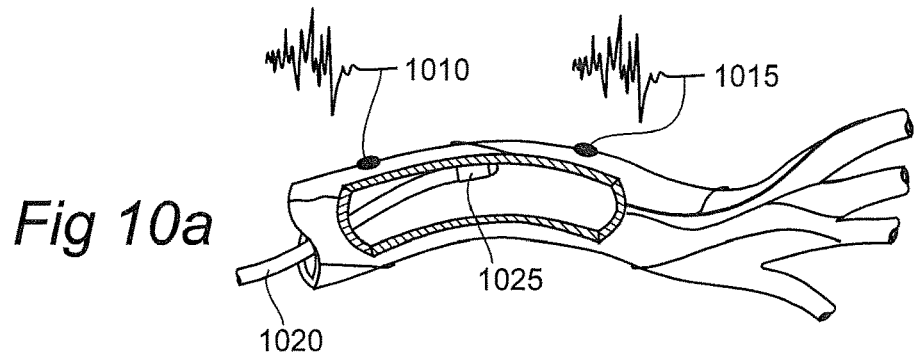
FIGS. 10a-d show aspects of non-limiting examples of monitoring methods in accordance with the present disclosure.

FIG. 10*a* shows a lumen (i.e. a vessel, a vein, an artery, a renal artery, etc.) prior to a surgical process. Two sensing sites are shown, distal 1015 and proximal 1010 to the intended surgical site. An ablation catheter tip 1020 (e.g. although shown as a separate unit, it may be included in an associated microfinger array as a sensing tip in accordance with the present disclosure) including an ablation electrode 1025 is placed in contact with the tissues between the sensing sites. One or more sensing tips may be placed at the sensing sites 1010, 1015, among others, as well as optionally at the surgical site (i.e. to perform a combination of sensing and procedures). Prior to initiation of the surgical procedure, nervous activity may be detected at both sensing sites 1010, 1015. In aspects, the correlation between the electrophysiological signals (i.e. neurological signals, electromyographic signals, mechanical myographic signals, etc.) may be relatively high prior to initiation of a surgical procedure. In aspects, the correlation between the electrophysiological signals may include the step of extracting a portion of each signal that is substantially common to both signals for analysis.

Figure 10B:
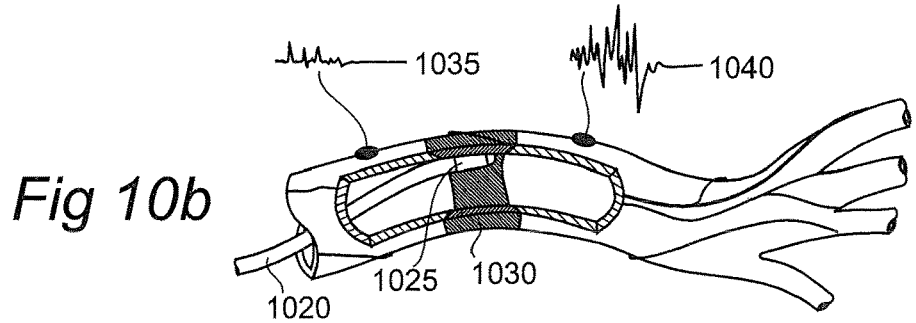

FIG. 10*b* shows a lumen (i.e. a renal artery) after a surgical ablation process. Two sensing sites are shown, distal 1040 and proximal 1035 to the surgical site. An ablation catheter tip 1020 (e.g. although shown as a separate unit, it may be included in an associated microfinger array as a sensing tip in accordance with the present disclosure) equipped with an ablation electrode 1030 is placed in contact with the tissues between the sensing sites. The ablation catheter tip 1020 has been employed as part of a surgical procedure to form an ablation zone 1030, in this case shown substantially around the circumference of the arterial wall around the surgical site forming the ablation zone 1030. After completion of the ablation procedure, nervous activity may no longer be detected at one or more of the sensing sites 1035. In this example, the ablation procedure has substantially blocked afferent nerve traffic from proceeding through the ablation zone 1030. In aspects, efferent nerve traffic may still be detectable at the proximal sensing site 1035, and afferent nerve traffic may still be detectable at the distal sensing site 1040. The correlation between the resulting signals may be used to quantify the state of the ablation process, the extent of denervation, etc.

In aspects, the above method and variations thereof may be used to extract the afferent from the efferent nerve traffic in the vicinity of a surgical site of interest. In aspects, the surgical procedure may include the application of energy to the surgical site in a substantially low dosage so as to temporarily inhibit function of the neurological anatomy in the vicinity thereof. In one non-limiting example, the energy may be used to heat the local tissues to a temperature of greater than 40 C, 45 C, 50 C so as to form the temporary block. Signals obtained by the distal and proximal sensing sites 1035, 1040 may be used to determine when the block has occurred, how the block has affected the traffic, and to distinguish, post block, information about the efferent and afferent nerve traffic in the vicinity of the surgical site.

In aspects, following a temporary block, if the procedure has favorably altered the neurological traffic, a more durable procedure may be completed (i.e. an ablation procedure, a chemical denervation, a thermal ablation process, a radiation based ablation, etc.). Such an approach may be advantageous for safely determining the ideal targets for a surgical procedure, for minimizing damage to the surrounding tissues in completing a denervation procedure, and the like.

Figure 10C:
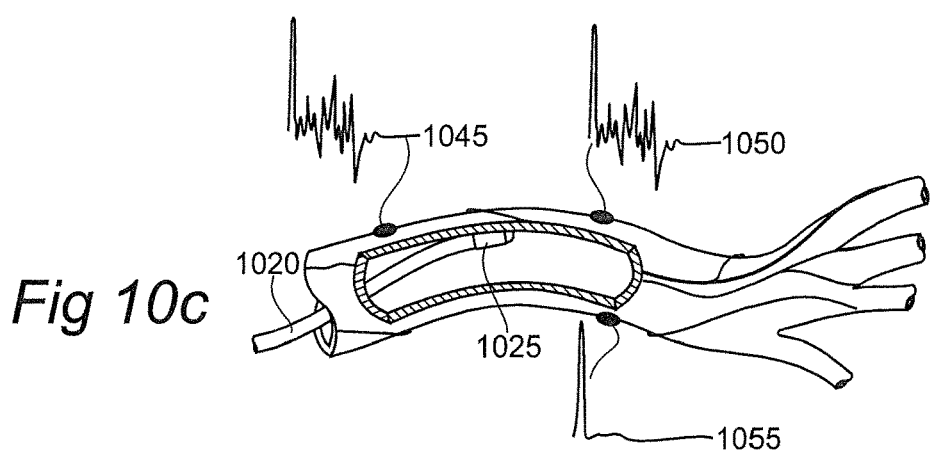

FIG. 10*c* shows a lumen (i.e. a renal artery) prior to a surgical process. Two sensing sites are shown, distal 1050 and proximal 1045 to the intended surgical site and a pacing site 1055 is shown located to one side of the intended surgical site. An ablation catheter tip 1020 (e.g. although shown as a separate unit, it may be included in an associated microfinger array as a sensing tip in accordance with the present disclosure) is placed in contact with the tissues between the sensing sites. One or more sensing tips may be placed at the sensing sites 1045, 1050, among others, as well as optionally at the surgical site (i.e. to perform a combination of sensing and procedures). Prior to initiation of the surgical procedure, both a pacing signal 1055 as well as associated nervous activity may be reliably detected at both sensing sites 1045, 1050. The pacing signal 1055 may be used to determine a transmission velocity along the associated anatomy between the pacing site 1055 and each of the sensing sites 1045, 1050, may be used to determine the transmission characteristics of the anatomy between sites, etc. In aspects, the coherence between the electrophysiological signals (i.e. neurological signals, electromyographic signals, mechanical myographic signals, etc.) may be relatively high prior to initiation of a surgical procedure. In aspects, the coherence in combination with the pacing signal may be advantageous in extracting the relevant information to make an assessment of neurological function quickly and reliably, even in the presence in considerable background noise, movement, and physiologically relevant neurological activity.

In aspects, the step of evaluating the coherence between the electrophysiological signals may include the step of extracting a portion of each signal that is substantially common to both signals for analysis.

Figure 10D:
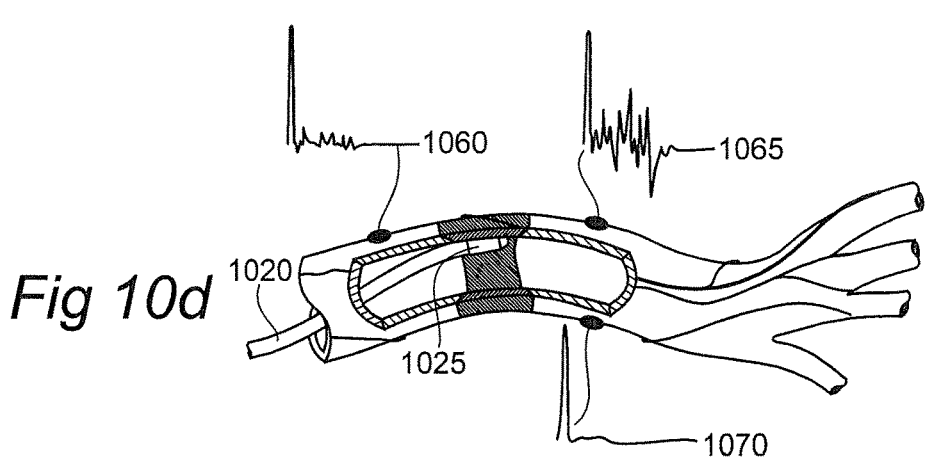

FIG. 10*d* shows a renal artery after a surgical ablation process. Two sensing sites are shown, distal 1065 and proximal 1060 to the surgical site and a pacing site 1070 is shown located to one side of the intended surgical site. An ablation catheter tip 1020 (e.g. although shown as a separate unit, it may be included in an associated microfinger array as a sensing tip in accordance with the present disclosure) with an ablation electrode 1025 is placed in contact with the tissues between the sensing sites 1060, 1070. The ablation catheter tip 1020 has been swept around the circumference of the arterial wall around the intended surgical site forming an ablation zone 1030. After completion of the ablation procedure, nervous activity may no longer be detected at one or more of the sensing sites 1060, 1065 even under the continued action of the pacing signal 1070.

In aspects, one or more of the distal sensing 1015, 1040, 1050, 1065, proximal sensing 1010, 1035, 1045, 1060, pacing 1055, 1070, and surgical procedure (i.e. formation of a blocked region, an ablation zone 1030, etc.) may be completed by one or more sensing tips each in accordance with the present disclosure.

FIGS. 11*a*-*f* show some non-limiting examples of ablation patterns applied to a renal artery in accordance with the present disclosure.

FIG. 11*a* shows a lumen 1105 (i.e. a tubule, a vessel, an artery, a vein, a renal artery, etc.) prior to the application of a surgical procedure thereto. As outlined in the Figure, a range of neurological structures (i.e. nerve plexuses) 1110, 1115, 1120, are visible within the wall and surrounding adventitia of the lumen 1105. In aspects, the lumen 1105 may provide a conduit for flow of a fluid (i.e. blood, bile, lymph, urine, feces, etc.), and to interconnect one or more organs, and or aspects of an organ (i.e. an intra-organ vessel).

FIG. 11b shows the lumen (i.e. the renal artery) with a circumferentially ablated region 1125 generated by a micro surgical tool in accordance with the present disclosure. Sensing tips located to either side or within the ablation zone 1125 may be used to confirm effective ablation, control the ablation process itself, for decision making related to the size and placement of the ablation site, to limit the overall amount of damage caused by the ablation procedure, or the like. In this non-limiting example, the associated ablation zone 1125 may be produced by collective activation of a plurality of sensing tips, arranged around the circumference of the lumen 1105, by swept motion of one or more sensing tips during a procedure, or the like.

FIG. 11c shows the lumen (i.e. the renal artery) after a selectively targeted nerve bundle 1127 has been ablated by a micro surgical tool in accordance with the present disclosure. Sensing tips included in the micro surgical tool may have been used to locate target tissues for ablation, monitor the ablation process itself, to avoid ablation of nerve bundles that are not to be surgically treated, to confirm effective ablation, and to limit the overall amount of damage caused by the ablation procedure. In this non-limiting example, the nerve bundle 1127 is ablated at local sites 1130 along the length thereof so as to limit damage to the surrounding tissues. In aspects, such ablation profiles may be formed during collective activation of a plurality of sensing tips each in accordance with the present disclosure, via selective ablation of tips during a longitudinal sweeping process, via selective ablation of tips during a tracking process, combinations thereof, or the like.

FIG. 11d shows the lumen (i.e. renal artery) after a group of selectively targeted nerve bundles 1132, 1134 have been ablated by a micro surgical tool in accordance with the present disclosure. In aspects, sensing tips included in the micro surgical tool may have been used to locate target tissues for ablation, monitor the ablation process itself, to avoid ablation of nerve bundles that are not to be surgically treated, to confirm effective ablation, and to limit the overall amount of damage caused by the ablation procedure. In this non-limiting example, the nerve bundles 1132, 1134 are ablated at local sites 1135 along the length thereof so as to limit damage to the surrounding tissues. Local sites 1135 may be placed so as to minimize potential damage to nearby anatomical features, which may not be intended targets for the surgical procedure.

FIG. 11e shows the lumen (i.e. renal artery) after a selectively targeted nerve bundle 1142 has been ablated by a micro surgical tool in accordance with the present disclosure. In aspects, sensing tips included in the micro surgical tool may have been used to track the targeted tissues as the ablation process is occurring (so as to establish an ablation path along the target tissues), locate target tissues for ablation, monitor the ablation process itself, to avoid ablation of nerve bundles that are not to be surgically treated, to confirm effective ablation, and to limit the overall amount of damage caused by the ablation procedure. In this non-limiting example, the nerve bundle 1142 is ablated along a continuous strip 1140 as followed with guidance from the sensing tips. Such a long stretch of ablated tissue may be employed to limit the potential for regeneration after the surgical procedure has been completed. In aspects, feedback from signals obtained from one or more sensing tips may be used to guide the surgical hardware during the surgical procedure (i.e. ablation, chemical substance delivery, etc.).

FIG. 11f shows the lumen (i.e. renal artery) after selectively targeted nerve bundles 1152, 1154, 1156 have been ablated by a micro surgical tool in accordance with the present disclosure. In aspects, the sensing tips included in the micro surgical tool may have been used to locate target tissues for ablation, to identify tissues for ablation, monitor the ablation process itself, to avoid ablation of nerve bundles that are not to be surgically treated, to confirm effective ablation, and to limit the overall amount of damage caused by the ablation procedure. A substantially helical tool path 1150 is shown, as the micro surgical tool traced around the walls of the renal artery during the ablation procedure. In this non-limiting example, the nerve bundles 1152, 1154, 1156 are ablated at a plurality of local sites 1145 along the length thereof so as to limit damage to the surrounding tissues. In aspects, the targeted neuroanatomical structures 1152, 1154, 1156 may be treated along the length thereof in order to control the post-surgical regrowth rate, or the like.

FIG. 11f shows a lumen 1160 (i.e. a vessel, an artery, a renal artery, a vein, a tubule, etc.) after a selectively targeted treatment zones 1175, 1180, 1185 have been formed around target anatomical structures 1065, 1067, 1069 by a micro surgical tool in accordance with the present disclosure. Target neurological structure 1165, perhaps connecting one or more structures 1170 in the vicinity of the lumen 1160 to one or more external organs, ganglia, or the like, that are somewhat removed from the lumen 1160 may be targeted as well during such procedures. In aspects, sensing tips included in the micro surgical tool may have been used to track the targeted tissues as the surgical process is occurring (so as to establish a treatment path in the vicinity of the target tissues), locate target tissues for treatment, monitor the treatment process itself, to avoid unintentional treatment of nerve bundles that are not to be surgically treated, to confirm effective treatment, and to limit the overall amount of damage caused by the treatment procedure. In this non-limiting example, the target anatomical structures 1165, 1167, 1169 are treated along one or more pathways 1177, 1182, 1187 as followed with guidance from one or more of the sensing tips (or via collective local treatment by a collection of sensing tips). Such stretches and strategic placement of treatment zones 1175, 1180, 1185 may be employed to limit the potential for regeneration after the surgical procedure has been completed. In aspects, feedback from signals obtained from one or more sensing tips may be used to guide the surgical hardware during the surgical procedure (i.e. ablation, chemical substance delivery, cryoablation, energy delivery, abrasion, etc.).

FIG. 12a shows a schematic diagram of a micro surgical tool 1210 deployed at a surgical site in accordance with the present disclosure. The micro surgical tool 1210 is shown deployed into a renal artery 1202 of a subject having passed through a superior or inferior approach (brachial or femoral arteries), via aortic artery 1205 and into the renal artery 1202 (or to the mouth thereof). The micro surgical tool 1210 includes a delivery catheter 1224 and a microfinger array 1212 in accordance with the present disclosure, shown in contact with the walls of the renal artery 1203 (i.e. biased towards, in controlled contact with, penetrating into, etc.). Connected to the microfinger array 1212 via a guiding arm 1215 is a local control circuit 1220 in accordance with the present disclosure. In aspects, the guiding arm 1215 may include one or more electrical interconnects, one or more structural elements, a conduit, or the like coupled to the microfinger array 1212 and/or the local control circuit 1220.

The control circuit 1220 may route signal traffic to and from the microfinger array 1212, etc. The schematic further depicts application of RF current 1221 applied locally between sensing tips in the microfinger array 1212 as well as an alternative RF current 1223 between one or more sensing tips in the microfinger array 1212 and an external electrode (not explicitly shown). The catheter 1224 may be coupled to an operator 1226, a controller, a signal conditioning circuit, or the like for controlling the microfinger array 1212 during a procedure. In aspects, the microfinger array 1212 may be advanced and/or retracted 1227, along the lumen 1203 and/or rotated 1229 around the circumference of the lumen 1203 during procedures related to searching for anatomical sites of interest, performing sensing, mapping, surgical treatments, ablation, or the like.

FIG. 12*b* shows a schematic diagram of a micro surgical tool 1230 deployed at a surgical site in accordance with the present disclosure. The micro surgical tool 1230 is shown deployed into a renal artery 1202 of a subject having passed through a superior or inferior approach (brachial or femoral arteries), via aortic artery 1205 and into the renal artery 1202 (or to the mouth thereof). The micro surgical tool 1230 includes a delivery catheter 1232 and a microfinger array 1234 in accordance with the present disclosure, shown in contact with the walls of the renal artery 1203 (i.e. biased towards, in controlled contact with, penetrating into, etc.). In this, non-limiting example, the microfinger array 1234 is configured as a longitudinal wire cage in accordance with the present disclosure. Such a configuration may be advantageous to maintain contact with the lumen walls during a procedure without inhibiting flow of fluids through lumen. Connected to the microfinger array 1234 via a guiding arm 1238 is a local control circuit 1236 in accordance with the present disclosure. In aspects, the guiding arm 1238 may include one or more electrical interconnects, one or more structural elements, a conduit, or the like coupled to the microfinger array 1234 and/or the local control circuit 1236. The micro-surgical tool 1230 is also configured to accommodate, or includes a guide wire 1240 configured to assist with guiding the microfinger array 1234 to the target anatomical site. The microfinger array 1234 may be coupled to a distal ringlet 1241 or equivalent feature, configured to accommodate the passage of the guide wire 1240 there through during the procedure. In aspects, the control circuit 1236 may route signal traffic to and from the microfinger array 1234, etc. The schematic further depicts application of RF current 1243 applied locally between sensing tips in the microfinger array 1234 as well as an alternative RF current 1245 between one or more sensing tips in the microfinger array 1234 and an external electrode (not explicitly shown). The catheter 1236 and/or guiding arm 1238 may be coupled to an operator 1226, a controller, a signal conditioning circuit, or the like for controlling the microfinger array 1234 during a procedure. In aspects, the microfinger array 1234 may be advanced and/or retracted 1247, along the lumen 1203 and/or expanded/contracted 1238 as part of a procedure, a deployment, and/or a retraction procedure within the lumen 1203 during procedures related to searching for anatomical sites of interest, performing sensing, mapping, surgical treatments, ablation, or the like.

FIG. 12*c* shows a schematic diagram of a micro surgical tool 1250 deployed at a surgical site in accordance with the present disclosure. The micro surgical tool 1250 is shown deployed into a renal artery 1202 of a subject having passed through a superior or inferior approach (brachial or femoral arteries), via aortic artery 1205 and into the renal artery 1202 (or to the mouth thereof). The micro surgical tool 1250 includes a delivery catheter 1258 and a plurality of microfinger arrays 1252, 1254 each in accordance with the present disclosure, shown in contact with the walls of the renal artery 1203 (i.e. biased towards, in controlled contact with, penetrating into, etc.). In this, non-limiting example, the microfinger arrays 1252, 1254 are configured as a radially biased flexural springs, in accordance with the present disclosure. Such a configuration may be advantageous to maintain contact with the lumen walls during a procedure without inhibiting flow of fluids through lumen, to accommodate a wide range of anatomical features, to maintain a relatively constant bias force on the lumen walls 1203 during a procedure, for simple deployment/retraction, combinations thereof, or the like. Connected to the microfinger arrays 1252, 1254 via one or more guiding arms 1256, 1257 is a local control circuit 1260 in accordance with the present disclosure. In aspects, the guiding arm(s) 1256, 1257 may include one or more electrical interconnects, one or more structural elements, a conduit, or the like coupled to the microfinger arrays 1252, 1254 and/or the local control circuit 1260. The micro-surgical tool 1250 may also be configured to accommodate, and/or include a guide wire (not explicitly shown) configured to assist with guiding the microfinger arrays 1252, 1254 to the target anatomical site. In aspects, one or more of the guiding arms 1256, 1257 may be configured so as to retract and or advance along the microsurgical tool 1250 with respect to the microfinger arrays 1252, 1254 so as to cover and/or expose one or more of the microfinger arrays 1252, 1254 during a retraction and/or deployment process. In aspects, the control circuit 1260 may route signal traffic to and from one or more of the microfinger arrays 1252, 1254, etc. The schematic further depicts application of RF current 1261 applied locally between sensing tips in the microfinger arrays 1252, 1254 as well as an alternative RF current 1263 between one or more sensing tips in the microfinger arrays 1252, 1254 and an external electrode (not explicitly shown). The catheter 1260 and/or guiding arm(s) 1256, 1257 may be coupled to an operator 1226, a controller, a signal conditioning circuit, or the like for controlling the microfinger arrays 1252, 1254 during a procedure. In aspects, the microfinger arrays 1252, 1254 may be advanced and/or retracted 1265, along the lumen 1203 and/or deployed or retracted by movement 1267 of one or more guiding arms 1256, 1257 during deployment, and/or a retraction procedure within the lumen 1203 during procedures related to searching for anatomical sites of interest, performing sensing, mapping, surgical treatments, ablation, or the like. In aspects, the microsurgical tool 1250 may be advanced after deployment of the microfinger arrays 1252, 1254 so as to strongly bias and/or penetrate one or more sensing tips in the microfinger arrays 1252, 1254 into the wall 1203 of the lumen 1205 during a procedure.

FIG. 12*d* shows a schematic diagram of a micro surgical tool 1270 deployed at a surgical site in accordance with the present disclosure. The micro surgical tool 1270 is shown deployed into a renal artery 1202 of a subject having passed through a superior or inferior approach (brachial or femoral arteries), via aortic artery 1205 and into the renal artery 1202 (or to the mouth thereof). The micro surgical tool 1270 includes a delivery catheter 1272 and a plurality of sensing tips 1274 arranged over a balloon 1275 each in accordance with the present disclosure, shown in contact with the walls of the renal artery 1203 (i.e. biased towards, in controlled contact with, penetrating into, etc.). In this, non-limiting example, one or more of the sensing tips 1274 maybe arranged along the balloon 1275 walls so as to contact the lumen wall 1203 during and/or after deployment. Such a configuration may be advantageous for isolating one or more of the sensing tips 1274 from the fluid which would normally flow through the lumen 1202. Connected to the balloon 1275 and one or more of the sensing tips 1274, via a guiding arm 1277 is a local control circuit 1280 in accordance with the present disclosure. In aspects, the guiding arm 1277 may include one or more electrical interconnects, one or more structural elements, a conduit for delivery/removal of fluid to/from the balloon 1275, or the like coupled to the sensing tips 1274 and/or the local control circuit 1280. The micro-surgical tool 1270 may also be configured to accommodate, and/or include a guide wire (not explicitly shown) configured to assist with guiding the balloon 1275 to the target anatomical site. In aspects, the balloon 1275 and/or guiding arm 1277 may be coupled to a distal ringlet 1282 or equivalent feature, configured to fasten the balloon to the guiding arm 1277 and/or to accommodate the passage of the guide wire 1240 there through during the procedure. In aspects, the guiding arm 1277 may be configured so as to retract and or advance along the microsurgical tool 1270 with respect to the balloon 1275 so as to cover and/or expose one or more of the sensing tips 1274 during a retraction and/or deployment process. In aspects, the control circuit 1280 may route signal traffic to and from one or more of the sensing tips 1274, etc. The schematic further depicts application of RF current 1281 applied locally between sensing tips 1274 as well as an alternative RF current 1283 between one or more sensing tips 1274 and an external electrode (not explicitly shown). The catheter 1272 and/or guiding arm 1277 may be coupled to an operator 1226, a controller, a signal conditioning circuit, or the like for controlling the sensing tips 1274 during a procedure. In aspects, the balloon 1275 may be repositioned 1285 along the lumen 1203 and/or expanded or contracted 1287 during deployment, and/or a retraction procedure within the lumen 1203 during procedures related to searching for anatomical sites of interest, performing sensing, mapping, surgical treatments, ablation, or the like.

FIG. 13 shows a schematic diagram of interaction between one or more macroelectrodes 1302, 1304, 1306 (i.e. not limited to three, could be a range of possibilities) and a micro surgical tool 1310 deployed at a surgical site in accordance with the present disclosure. The abdomen 1301 of a subject is shown with an internally placed micro surgical tool 1310 (dotted line) located with the tip 1315 in a renal artery of the subject. When a suitable target site for an ablation process is determined, the electrical impedance (e.g. DC impedance, AC impedance, real, imaginary, complex impedance spectra, etc.) between elements of the network formed by one or more sensing tips 1315 included in the micro surgical tool 1310, one or more macroelectrodes 1302, 1304, 1306 placed on the body of the patient, pushed up against the patient, located along the catheter wall of the micro surgical tool, placed within the patient (perhaps endoscopically, via a catheterization procedure, etc.) may be monitored. Such relational impedance measurements are depicted diagrammatically with arrows 1321, 1323, 1325, 1331, 1333, 1335 between elements 1302, 1304, 1306, 1310, 1315 of the network in FIG. 13.

Based upon the impedances in the associated network, an RF ablation current may be applied between two or more elements 1301, 1304, 1306, 1310, 1315 thereof. In one non-limiting example, each element 1301, 1304, 1306, 1310, 1315 of the network may include a controllable impedance circuit. The impedance control circuits may be used to draw a portion of the RF current into/out of the associated element 1301, 1304, 1306, 1310, 1315. In this sense, local control of the RF current at the sensing tips 1315 may be more precisely controlled. Electric field strengths, current flow, etc. may be monitored at any element 1301, 1304, 1306, 1310, 1315 of the network so as to determine the RF current flow path into the local tissues of the target anatomy (i.e. into a wall of a lumen, a renal artery, etc.).

Figure 14:
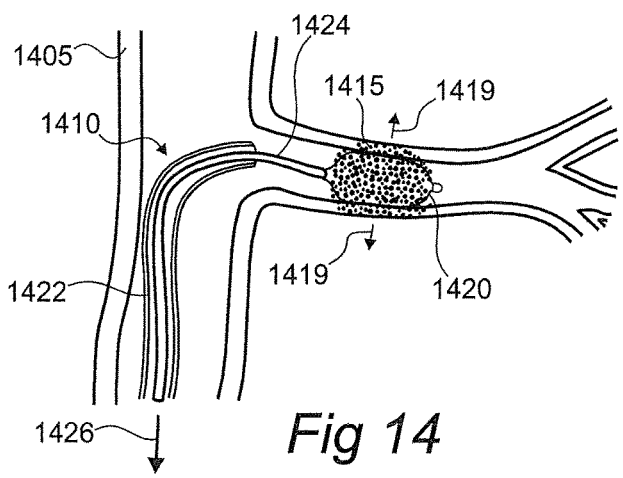
FIG. 14 shows aspects of a micro balloon catheter deployed at a surgical site in accordance with the present disclosure.

FIG. 14 shows a micro balloon catheter 1410 deployed at a surgical site in accordance with the present disclosure. In this non-limiting example, the micro balloon catheter 1410 is shown deployed into a renal artery 1402 of a subject having passed through a superior or inferior approach (brachial or femoral arteries), via aortic artery 1405 and into the renal artery 1402 (or to the mouth thereof). The micro balloon catheter 1410 is shown with a layer of indicating agents 1415 and/or contrast agent coated onto the balloon 1420 thereof. The micro balloon catheter 1410 is shown as placed within the renal artery 1402 of a subject, in an inflated state. In this state, the indicating agents 1415 and/or contrast agents are released 1419 (i.e. via diffusion, active transport, etc.) into the surrounding tissues for later use during a surgical procedure. In aspects, the micro balloon catheter 1410 may include one or more sensory tips, a delivery catheter 1422, a guiding arm 1424, coupled to the balloon 1420 in accordance with the present disclosure. The catheter 1422 may be coupled to an operator 1426, a controller, a signal conditioning circuit, or the like for controlling the balloon 1420 during a procedure. In aspects, the indicating agent 1415 may be configured so as to change chromatic and/or photochemical properties in the presence, when bound to, or when incorporated into the target anatomy.

Figure 15A:
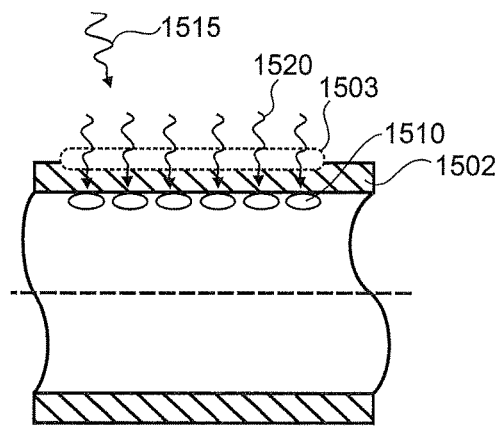
FIGS. 15a-b show aspects of an array of optical micro-sensing tips and a collective response therefrom in accordance with the present disclosure.
Figure 15B:
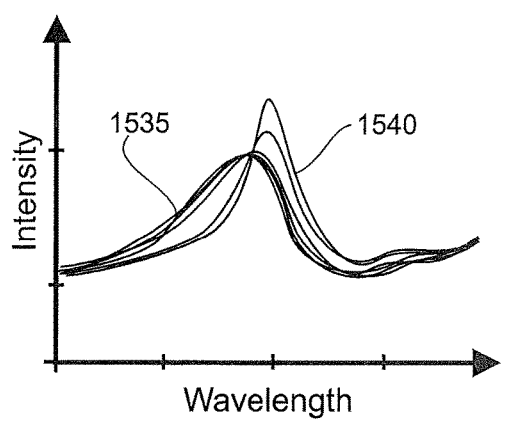

FIGS. 15a-b show aspects of non-limiting examples of optical microsensing tips 1510 and a collective response therefrom in accordance with the present disclosure. FIG. 15a shows an array of optical microsensing tips 1510 biased towards the wall 1501 of a vessel. The optical microsensing tips 1510 are configured to receive from and/or emit energy into the adjacent tissues of the wall 1501. In aspects, an external light source 1515 may also provide light towards the surgical site (i.e. vessel walls 1501). In aspects, energy 1520 passing through an anatomical site of interest 1503 may be accepted by one or more of the optical microsensing tips 1510, each configured to generate a signal therefrom. In aspects, the microsensing tips 1510 may include a fiber optic element coupled to a remote light source and/or photodetector. Such a configuration may be coupled with the indicating agents described in FIG. 15 (i.e. so as to locate the target anatomy as part of a surgical procedure). In aspects, the indicating agent 1415 may be configured so as to change chromatic and/or photochemical properties in the presence, when bound to, or when incorporated into the target anatomy 1503, thus being detectable by one or more optical microsensing tips 1510.

FIG. 15b shows a spectral response of the light received by the optical microsensing tips 1510 and that emitted by an external light source. The detected signals 1535, 1540 may be used to determine the location of target tissues in the vessel wall. In aspects, the optical microsensing tips 1510 may include one or more electrode elements so as to selectively and locally ablate target tissues based on the response of the sensed signals 1535, 1540.

Figure 16:
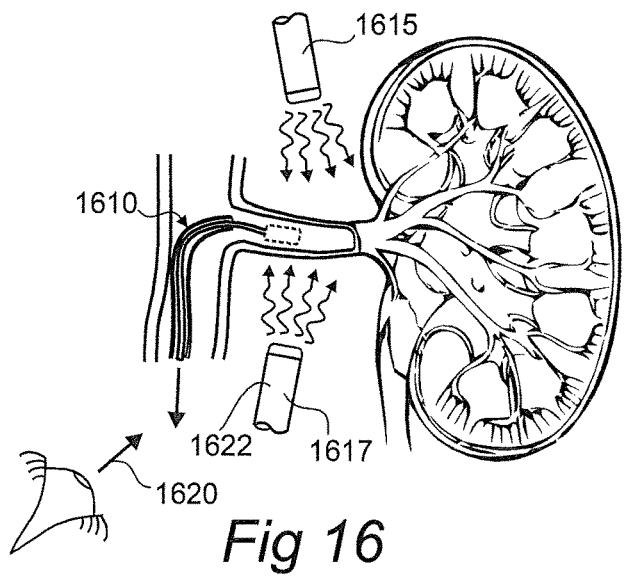
FIG. 16 shows aspects of a combination catheterization and endoscopic procedure on a renal artery in accordance with the present disclosure.

FIG. 16 shows a combination catheterization and endoscopic procedure on a renal artery in accordance with the present disclosure. A micro surgical tool 1610 in accordance with the present disclosure is shown as placed into the renal artery of a subject. One or more endoscopically placed light sources 1615, 1617 may be shone at the renal artery. In aspects, the light sources 1615, 1617 may be multi-band sources, broadband sources, narrow band sources, modulated, or any combination thereof. In aspects, the micro surgical 1610 tool may include one or more optical microsensors to receive such light, the processed signals used to determine the location of target tissues in the renal artery. In aspects, the microsurgical tool 1610 may include one or more sensing tips in accordance with the present disclosure to selectively treat target anatomy based on the determined locations thereof. An optional endoscopically placed camera 1620 is also shown. In aspects, the camera 1620 may include a light source. The camera 1620 may be used as part of a feedback mechanism to control placement of the micro surgical tool 1610 in the renal artery. In aspects, the camera 1620 may use a range of light sources to elicit placement information of target anatomy (perhaps in combination with indicating/contrast agents in accordance with the present disclosure), placement of the micro surgical tool 1610 within the renal artery, and/or monitoring of the surgical procedure (i.e. ablation procedure, chemical denervation, chemical deployment, etc.). Such a feedback mechanism may be used to precisely guide the micro surgical tool 1610 during a surgical procedure (i.e. ablation procedure, etc.). In one non-limiting example the camera 1620 and/or a light source 1615, 1617 may include a macroelectrode in accordance with the present disclosure.

Figures 17A, 17B, 17C:
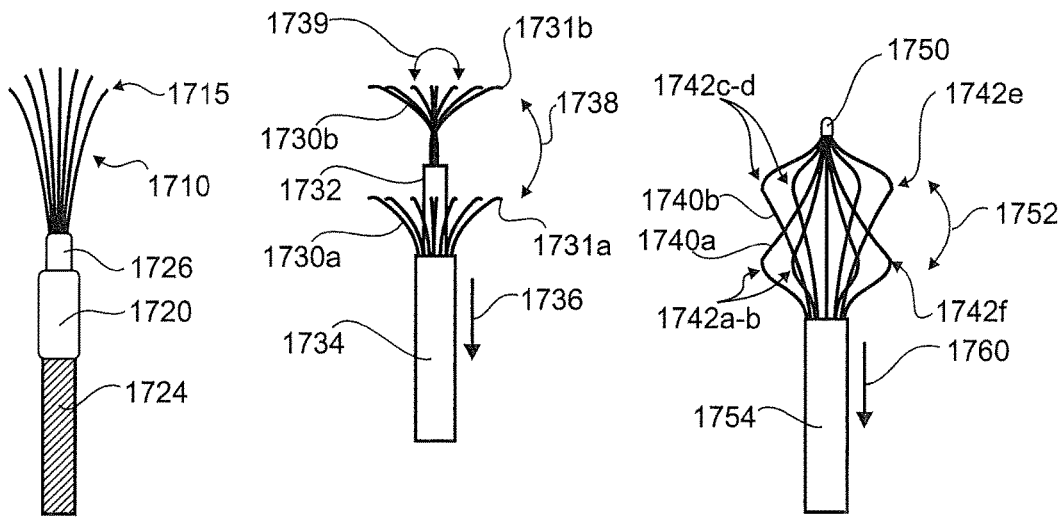
FIGS. 17a-c show aspects of micro surgical tools in accordance with the present disclosure.

FIG. 17*a* shows a schematic diagram of aspects of a micro surgical tool in accordance with the present disclosure. The micro surgical tool includes a plurality of microfingers 1710 equipped with sensing tips 1715 in accordance with the present disclosure, a local control circuit 1720 (optionally located near to the tip of the micro surgical tool) in accordance with the present disclosure, and a guiding arm 1726 and a delivery catheter 1724 to connect, both mechanically and electrically the tip of the tool to an operator, robot, etc. In aspects, the local control circuit 1720 may be located at the operating end of the catheter 1724 (i.e outside the body of a subject during use). Alternatively, additionally, or in combination a control circuit 1720 may be coupled to the microfingers 1710 directly, or via the guiding arm 1726 in order to communicate signals to or from the sensing tips 1715 during a procedure. In aspects, the microfingers 1710 may be configured so as to bend within the body of a subject (i.e. after a deployment process, etc.) so as to bias toward the walls of the anatomy of interest, etc. In aspects, the microfingers 1710 may be directed (i.e. like a pencil) towards the wall of an organ, and/or anatomical feature so as to form a plurality of microcontacts at each sensing tips, for the purposes of mapping, sensing, performing a treatment, etc. thereupon.

FIG. 17*b* shows a schematic diagram of aspects of a micro surgical tool in accordance with the present disclosure. The micro surgical tool includes a plurality of microfinger arrays 1730*a-b* equipped with sensing tips 1731*a-b*, a guiding arm 1732, and a delivery catheter 1734 each in accordance with the present disclosure. In aspects, the guiding arm 1732, one or more microfingers 1730*a-b*, and/or the catheter 1734 may include a control circuit in accordance with the present disclosure. In aspects, a local control circuit 1720 in accordance with the present disclosure may be located at the operating end of the catheter 1734 (i.e outside the body of a subject during use). Alternatively, additionally, or in combination a control circuit may be coupled to one or more of the microfingers 1730*a-b* directly, or via the guiding arm 1732 in order to communicate signals to or from the sensing tips 1731*a-b* during a procedure. In aspects, the microfinger arrays 1730*a-b* may be configured so as to bend within the body of a subject (i.e. after a deployment process, etc.) so as to bias toward the walls of the anatomy of interest, etc. In aspects, one or more of the microfingers 1730*a-b* may be configured so as to bend when heated to body temperature (i.e. so as to self-deploy during a procedure). In aspects, the guiding arm 1732 and/or the catheter 1734 (and/or a sleeve thereupon) may be retracted 1736 to initiate a deployment process so as to expose one or more of the microfingers 1730*a-b* and bring them into contact with the intended anatomy. In aspects, one or more sensing tips 1731*a-b* may be equipped with one or more electrodes for electrophysiological sensing, stimulation, and/or RF current delivery to the surrounding tissues. Thus signals may be monitored between 1738 sensing tips 1731*a-b* in different microfinger arrays 1730*a-b* or within 1739 the same microfinger array 1730*a*, 1730*b*. In aspects, the guiding arm 1732 and/or catheter 1736 may be adjustable so as to adjust the distance between microfinger arrays 1730*a-b* in the micro surgical tool tip.

FIG. 17*c* shows a schematic diagram of aspects of a micro surgical tool in accordance with the present disclosure. The micro surgical tool includes a longitudinal wire cage including a plurality of microfingers 1740*a-b*, with regions coupled to sensing tips 1742*a-f* in accordance with the present disclosure. Such a configuration may be advantageous to maintain contact between one or more sensing tips 1742*a-f* with the lumen walls during a procedure without inhibiting flow of fluids through lumen. In aspects, the micro-surgical tool may be configured to accommodate, or to include a guide wire (not explicitly shown) configured to assist with guiding wire cage to the target anatomical site. In aspects, the wire cage may be coupled to a distal ringlet 1750 or equivalent feature, configured to accommodate the passage of a guide wire there through during the procedure. The schematic further depicts application of RF current 1752 applied locally between sensing tips 1742*e,f* in the wire cage. The wire cage may be coupled to a delivery catheter 1754, perhaps coupled as a sleeve that can extend over the wire cage so as to force collapse thereof. In aspects, retraction 1760 of the delivery catheter 1754 may be used to deploy the wire cage during a procedure. The catheter 1754 and/or an enclosed guiding arm (not explicitly shown) may be coupled to an operator, a controller, a signal conditioning circuit, or the like for controlling the sensing tips 1742*a-f*, and/or the wire cage during a procedure. In aspects, the wire cage may be advanced and/or retracted, along a lumen (not explicitly shown) and/or expanded/contracted as part of a procedure, a deployment, and/or a retraction procedure within the lumen during procedures related to searching for anatomical sites of interest, performing sensing, mapping, surgical treatments, ablation, or the like.

In aspects, one or more sensing tips 1742*a-f* may be equipped with one or more electrodes for electrophysiological sensing, stimulation, and/or RF current delivery to the surrounding tissues. Thus signals may be monitored between sensing tips 1742*a-f*, between a sensing tip 1742*a-f* and an external electrode, etc.

In aspects, one or more sensing tips 1742*a-f* may be arranged longitudinally along the axis of the microsurgical tip, such that the sensing tips 1742*a-f* are biased against a lumen wall at site spaced along the longitudinal direction thereof upon deployment.

FIGS. 18*a-f* show aspects of non-limiting examples of micro surgical tools in accordance with the present disclosure.

Figure 18A:
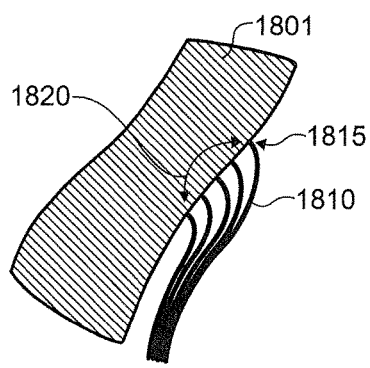
FIGS. 18a-f show aspects of non-limiting examples of micro surgical tools in accordance with the present disclosure.

FIG. 18*a* shows a microfinger array in accordance with the present disclosure. The array includes five microfingers 1810 each equipped with one or more sensory tips 1815 in accordance with the present disclosure. The microfingers 1810 and associated sensing tips 1815 are shown biased against a tissue surface 1801. Interaction between two of the sensing tips 1815 is depicted with an arrow 1820 in the diagram.

Figure 18B:
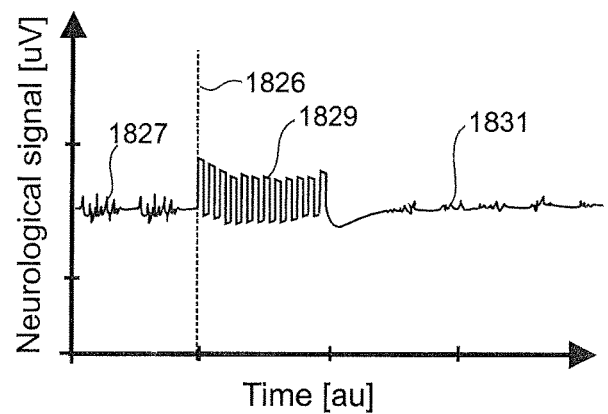

FIG. 18*b* shows a time series of data collected by several sensing tips 1815 in the microfinger array 1810. The neurological activity 1825 of a local tissue site is monitored 1827. At a ablation start time 1826, an ablation current 1829 is sent through one or more sensing tips 1815 and an altered neurological activity 1831 is confirmed afterwards.

Figure 18C:
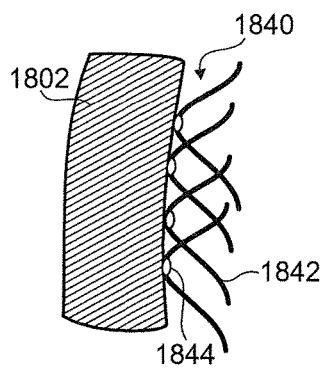

FIG. 18*c* shows an aspect of a mesh-like array 1840 of interwoven wires 1842 (i.e. microfingers in accordance with the present disclosure), with associated sensing tips 1844. The sensing tips 1844 may be arranged such that they contact the local tissues 1802 when the mesh 1840 is biased against the tissue 1802. In one non-limiting example, the mesh-like array 1840 may be formed from an interwoven group of superelastic wires (e.g. Nitinol wires, spring steel wires, etc.). The mesh 1840 may be formed as a sock, webbing, an arched structure, a donut, a net, etc. Upon deployment to the surgical site, the mesh 1840 may expand so as to contact the local tissues 1802 of interest. Electrical interconnects for the sensing tips 1844 may be provided via the wires 1842, routed along the wires 1842, etc. In on non-limiting example, substrates in accordance with the present disclosure may be interwoven instead of the wires 1842 as shown. Such substrates may be used to form a deployable mesh like structure complete with electrical interconnects, sensing tips 1844, distributed integrated circuits, etc.

Figure 18D:
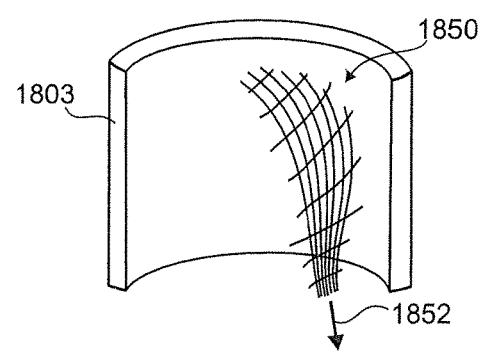

FIG. 18*d* shows aspects of a net like micro surgical tool in accordance with the present disclosure. The net like structure 1850 may be formed from one or more fibers, wires, ribbons, etc. Additionally, alternatively, or in combination the one or more net like structures 1850 may include a substrate in accordance with the present disclosure (e.g. a porous substrate material such as a silk structure, an elastomer, polymer, netting, fabric, fiber composite, etc.). In one non-limiting example, a silk-flexcircuit composite may form the net like structure 1850. In this example, the flexcircuit may be formed from materials as known to those skilled in the art, the flex circuit may be constructed such that substantial material, not occupied by electrical interconnects is removed (thus forming a loosely connected webbing of flexcircuit elements). The flexcircuit may thus be formed in an excessively thin form (e.g. less than 25 um, less than 10 um, less than 4 um, less than 1 um thick). A supporting material such as silk may be used to complete the substrate and form a functional, robust net like structure 1850 included in the micro surgical tool. The net like structure may be interconnected 1852 to a delivery catheter, an operator, a controller, one or more control circuits, etc. each in accordance with the present disclosure.

The micro surgical tool may include or be coupled with a micro balloon, the micro balloon configured so as to bias the net up against the local tissues 1803.

Figure 18E:
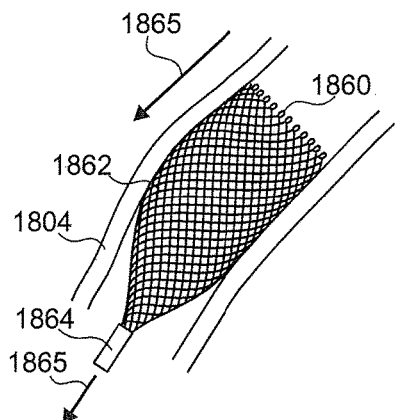

FIG. 18*e* shows a stent-like deployable micro surgical tool in accordance with the present disclosure. The stent-like micro tool 1862 may include a plurality of sensing tips 1860 electrically interconnected with the remainder of the micro surgical tool. The sensing tips 1860 may be positioned throughout the stent-like micro tool 1862. In one non-limiting example, the sensing tips 1860 may be generally positioned towards the end of the tool. The stent-like micro tool may be interconnected to a guiding arm 1864 for connection 1865 to an operator (not explicitly shown), controller, etc.

The stent-like micro tool may be inserted into a lumen 1804 past the intended surgical site. It may then be deployed so as to expand outwards and make contact with the lumen walls 1804. The micro-tool may then be dragged 1865 forward, sweeping along the walls of the vessel. In one non-limiting example, the sensing tips 1860 may be configured to monitor physiological parameters during this initial sweep (e.g. so as to map the local tissue properties). After the first sweep, the tool 1862 may be retracted and once again placed beyond the intended surgical site. It may then be deployed so as to expand outwards and make contact with the surgical site. The tool 1862 may then be dragged forward, sweeping along the walls of the vessel for a second time. During this second sweep, the sensing tips 1860 may be activated to locally ablate tissue at predetermined locations determined by the initial sweep. Sensory tips 1860 may further be monitored during ablation processes to ensure that the processes are sufficiently completed before further sweeping the stent-like micro tool 1862 though the vessel.

In another non-limiting example the stent-like micro tool 1862 may be inserted past the intended surgical site. It may then be deployed so as to expand outwards and make contact with the lumen wall 1804. The micro-tool 1862 may then be dragged forward, sweeping along the walls of the vessel 1804. The sensing tips 1860 may, in concert, monitor the local physiological properties of the tissues and selectively activated to locally ablate tissues. Thus both the functions of monitoring and ablation may be completed in a single sweep.

The stent-like micro tool 1862 may include any features described herein as they pertain to a microfinger in accordance with the present disclosure.

Figure 18F:
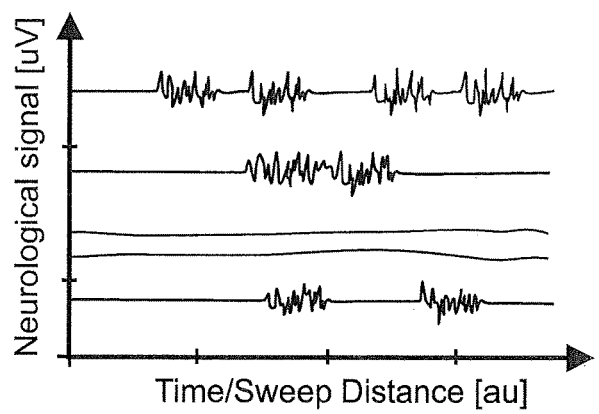

FIG. 18*f* shows a two dimensional graph, indicating the ablation profile of 5 sensing tips located in a stent-like micro tool in accordance with the present disclosure. The desired ablation profile may be predetermined (e.g. as determined by an initial sweep), or determined in concert during a sensing+ ablation sweep. As can be seen in the example shown, two of the sensing tips did not pass any target tissue in need of ablation during this sweep, thus an ablation procedure may be directed towards other sensing tips in the array so as to minimize damage to local tissues during the procedure.

Figure 19A:
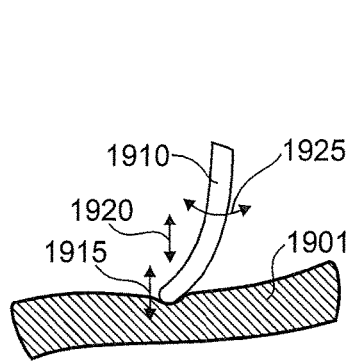
FIGS. 19a-b show aspects of a tonal sensing micro-tip and sample response in accordance with the present disclosure.
Figure 19B:
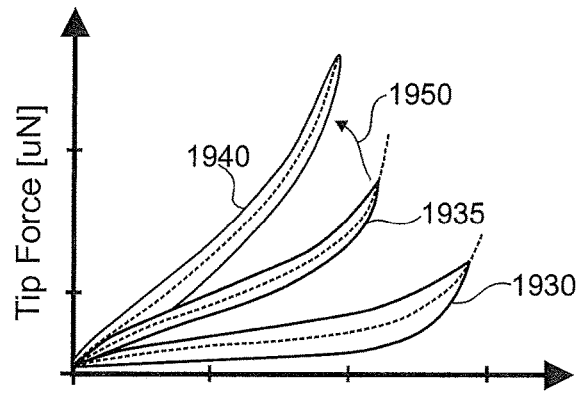

FIGS. 19*a-b* show a tonal sensing tip and sample response in accordance with the present disclosure. FIG. 19*a* shows a close up of an associated microfinger 1910 in accordance with the present disclosure. The microfinger 1910 includes an interfacial pressure sensor (at the tip, in accordance with the present disclosure) and/or a flexural sensor (along the length thereof, in accordance with the present disclosure). An excitation 1915, 1920, 1925 applied to the microfinger 1910 may be used to generate variable contact forces and contact deflections at the point of contact between the microfinger and a local tissue surface 1901. Signals obtained from the flexural sensor may be representative of the contact deflections that occur during the excitation period. Signals obtained from the interfacial pressure sensor may be representative of the contact forces that occur during the excitation period. The simultaneous monitoring of both signals, perhaps in combination with a compliance model for the microfinger 1810 may be useful for determining the local mechanical properties of the tissue in the vicinity of the contact point.

FIG. 19*b* shows a deflection force curve, generated by the microfinger 1810 described in FIG. 19*a* during an excitation session. The deflection/force relationships (e.g. mean relationships, hysteresis, frequency dependence, creep, strain hardening, etc.) may be used to determine the type of tissues 1801 in which the microfinger is in contact. As can be seen in the figure, a particularly soft relationship 1930 (low modulus of elasticity) may be associated with a potential tumor tissue. Healthy tissue may exhibit a modulus of elasticity within a known "good" range 1935, and the trend 1950 in elastic modulus that occurs as the tissue is ablated by a surgical procedure, may be followed to determine the extent of the ablation process. A successful ablation process may be qualified by a range of elastic modulus change 1940, as observed during the ablation process.

Figure 20A:
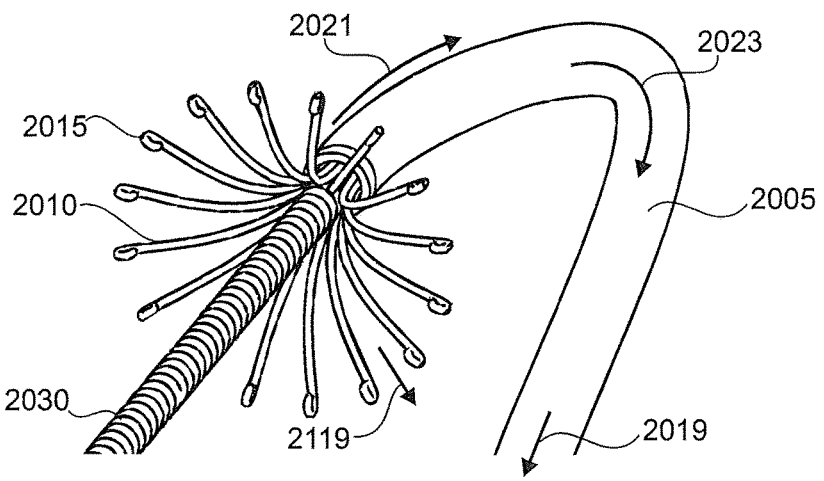
FIGS. 20a-b show aspects of surgical tools in accordance with the present disclosure.
Figure 20B:
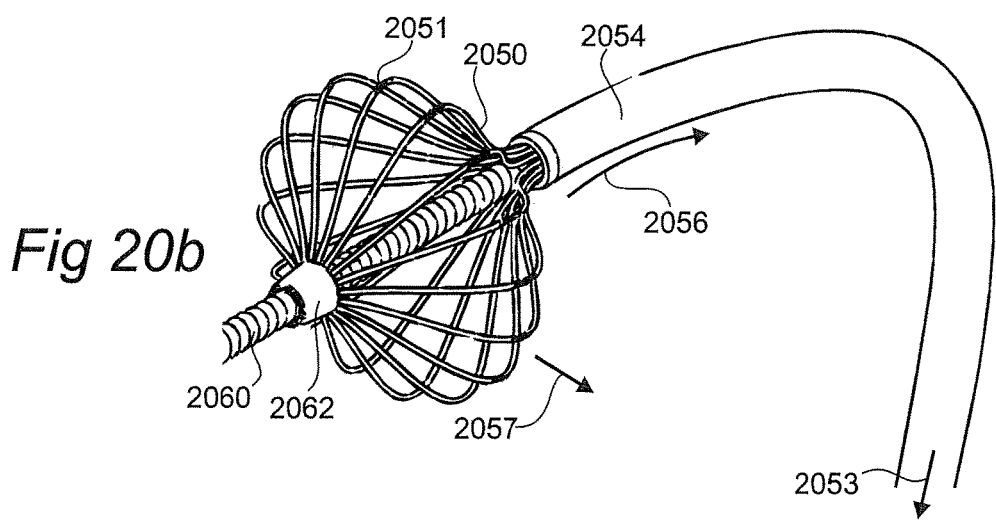

FIGS. 20a-b show aspects of surgical tools in accordance with the present disclosure. FIG. 20a shows a surgical tool including a delivery catheter 2005 in accordance with the present disclosure including an array of microfingers 2010, the microfingers 2010 connected 2011 through the catheter 2005 to an operating fixture, control circuit, signal conditioning circuit, hand held control unit, surgical robot, a coupling, or the like. The microfingers 2010 in accordance with the present disclosure are arranged along the inside of the delivery catheter 2005 and are arranged with a pre-biased shape, such that upon retraction 2021 of the catheter 2005, the microfingers 2010 may be deployed radially 2019 towards an anatomical site of interest (i.e. a surgical site, a tissue surface, a lumen wall, etc.). One or more of the microfingers 2010 may include one or more sensing tips 2015 in accordance with the present disclosure. In the non-limiting example shown, each sensing tip includes an electrode configured to interface with an anatomical site of interest. The catheter 2005 is configured to slide over an associated guide wire 2030, so as to be easily directed to a surgical site during an insertion procedure. In the non-limiting example shown, the microfingers 2010 include shaped tips (upon which the sensing tips 2015 are arranged). Such shaped tips may be advantageous to control the bias pressure against an anatomical site of interest (i.e. so as to prevent penetration, etc.). In aspects, one or more of the microfingers 2010 may terminate at a microneedle sensing tip in accordance with the present disclosure. Such a configuration may be advantageous to allow for controlled penetration of one or more sensing tips 2015 into the wall of a surgical site. In aspects, after deployment, the entire microfinger array 2010 may be drawn 2023 along the length of a lumen, so as to map the lumen, sweep monitor and ablate the lumen, assess the state of anatomy after a surgical procedure, combinations thereof, or the like.

FIG. 20b shows catheter 2005 in accordance with the present disclosure including a longitudinal wire cage including an array of microfingers 2010, the microfingers 2050 connected 2053 through a delivery catheter 2054 to an operating fixture, control circuit, signal conditioning circuit, hand held control unit, surgical robot, a coupling, or the like. The microfingers 2050 in accordance with the present disclosure are arranged along the inside of the delivery catheter 2054 with a range of pre-biased shapes, such that upon retraction 2056 of the delivery catheter 2054 or an over sheath coupled thereto, the microfingers 2050 may be deployed radially 2057 towards an anatomical site of interest (i.e. a surgical site, a tissue surface, a lumen wall, etc.) to form the wire cage. One or more of the microfingers 2050 may include one or more sensing tips 2051 in accordance with the present disclosure. In the non-limiting example shown, each sensing tip includes an electrode configured to interface with an anatomical site of interest. The catheter 2054 is configured to slide over an associated guide wire 2060, so as to be easily directed to a surgical site during an insertion procedure. In aspects, the wire cage may be coupled to a distal ringlet 2062 or equivalent feature, configured to accommodate the passage of a guide wire there through during the procedure.

In aspects, the microfingers 2050 may be arranged such the sensing tips 2051 are arranged so as to contact the lumen wall upon deployment.

Such a configuration may be advantageous to maintain contact between one or more sensing tips 2051 with the lumen walls during a procedure without inhibiting flow of fluids through lumen. In aspects, the wire cage may be advanced and/or retracted, along a lumen (not explicitly shown) and/or expanded/contracted as part of a procedure, a deployment, and/or a retraction procedure within the lumen during procedures related to searching for anatomical sites of interest, performing sensing, mapping, surgical treatments, ablation, or the like.

In aspects, one or more sensing tips 2051 may be equipped with one or more electrodes for electrophysiological sensing, stimulation, and/or RF current delivery to the surrounding tissues.

In aspects, one or more sensing tips 2051 may be arranged longitudinally along the axis of the microsurgical tip, such that the sensing tips 2051 are biased against a lumen wall at site spaced along the longitudinal direction thereof upon deployment.

Figure 21:
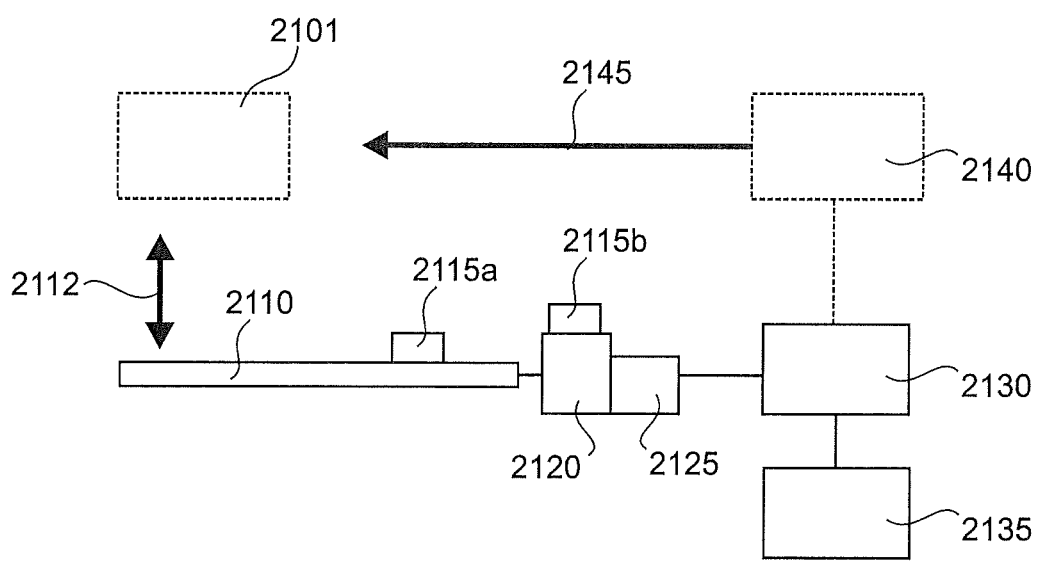
FIG. 21 shows aspects of a system for performing a surgical procedure in accordance with the present disclosure.

FIG. 21 shows aspects of a system for performing a surgical procedure in accordance with the present disclosure. The system is shown interfacing with a surgical site 2101 within a body, a subject, a patient, etc. The system includes a microsurgical tool 2110 in accordance with the present disclosure. During use, the microsurgical tool 2110 is configured to interact 2112 with the surgical site 2101 in accordance with the present disclosure. In aspects, the microsurgical tool 2110 may be coupled to a connector 2120, the connector providing a mechanical and electrical interface between the microsurgical tool 2110 and one or more other modules of the system. In aspects, the microsurgical tool may include an embedded local control circuit 2115a (a microcircuit, a switch network, a signal conditioning circuit, etc.) in accordance with the present disclosure. In aspects, the connector 2120 may include a local control circuit 2115b in accordance with the present disclosure. In aspects, the connector 2120 may be coupled to an operator input device 2125 (i.e. a foot pedal, an advancing slider, a torqueing mechanism, a recording button, an ablation button, etc.). In aspects, the connector 2120 may be coupled to a control unit 2130 configured to accept one or more signals from the microsurgical tool 2110, communicate one or more control signals thereto, send one or more pulsatile and/or radio frequency signals to the microcontroller, record one or more electrophysiological signals from the microsurgical tool, or the like.

In aspects, the control unit 2130 may be connected to a display 2135 configured to present one or more aspects of the recorded signals from the microsurgical tool to an operator, to present a map, at least partially dependent on the recorded signals, etc.

In aspects, the control unit 2130 may be coupled to a surgical subsystem 2140, the surgical subsystem 2140 configured to perform a surgical procedure 2145 to the surgical site 2101. Some non-limiting examples of suitable surgical procedures include an ablation, an excision, a cut, a burn, a radio frequency ablation, radiosurgery, an ultrasonic ablation, an abrasion, a biopsy, and delivery of a substance. The control unit 2130 may be configured to influence, direct, control, and/or provide feedback for one or more aspects of the surgical procedure 2140, based upon one or more of the electrophysiological signals conveyed by the microsurgical tool 2110.

Some non-limiting methods for performing a surgical procedure in accordance with the present disclosure are discussed herein.

In one non-limiting example, a method for addressing a surgical site within a vessel (e.g. an artery, a vein, a renal artery, a micro-vessel, etc.) is considered. The method includes, monitoring one or more local physiological signals (e.g. an evoked potential, a neurological activity, MSNA, EMG, MMG, extracellular signal, sympathetic tonal change, etc.) in accordance with the present disclosure at one or more measurement locations within the vessel to determine one or more reference signals; performing at least a portion of a surgical procedure (e.g. an ablation, an excision, a cut, a burn, an RF ablation, an abrasion, radiosurgery, an ultrasonic ablation, a biopsy, delivery of a substance, etc.) in accordance with the present disclosure at or near to one or more surgical locations (e.g. proximal, distal, remotely therefrom, and/or collocated with one or more of the measurement locations); monitoring one or more local physiological signals at one or more of the measurement locations to determine one or more updated signals; and comparing one or more reference signals with one or more updated signals to determine an extent of completion for the surgical procedure.

In aspects, the extent of completion may include a change, reduction and/or substantial elimination of at least a portion of one or more of the local physiological signals (e.g. reduction in amplitude of a frequency band, reduction in responsiveness, a change in a lag between measurement locations, a change in cross-talk between measurement locations, substantial elimination of the signal, etc.)

In aspects, the extent of completion may include measuring a change in coherence between two or more signals obtained from sites affected by the surgical procedure (i.e. from a first site distal to where the surgical procedure was performed, and from a second site proximal to where the surgical procedure was performed).

In aspects, the procedure may be to perform a temporary neurological block. In this aspect, the method may be used to separate afferent and efferent traffic from either side of the temporary block, for further analysis, diagnosis of disease, evaluation of neurological activity, or the like. In aspects, a temporary block may be followed by a more permanent block if the analysis demonstrates that such a substantially permanent block would be warranted.

The step of monitoring to determine an updated signal may be performed before, during, and/or after the step of performing at least a portion of the surgical procedure. In aspects, monitoring, stimulation, and ablation may be performed in succession and/or in parallel.

In aspects, the method may include sweeping one or more electrodes over the lumen wall while monitoring, stimulating, and/or ablating the surface thereof. In aspects, simultaneous monitoring and sweeping may be used to generate a map of neurological activity along the lumen wall.

The step of performing at least a portion of the surgical procedure may be repeated. Thus the method may be incrementally applied, so as to head towards completion in a stepwise process without excessive application of the surgical procedure.

The method may include waiting after performing at least a portion of the surgical procedure. Monitoring may be performed during the waiting procedure, perhaps so as to determine a recovery period for the local physiological signal (i.e. a time period over which the local physiological signal recovers). Such a recovery period may be an indication of the extent of completion.

In aspects, the method may include stimulating one or more stimulation locations (proximal, distal, remotely therefrom, and/or collocated with one or more of the measurement locations and/or the surgical locations). The step of stimulating may be coordinated with the step of performing at least a portion of the surgical procedure, and/or with the step of monitoring to determine a reference and/or updated signal. The stimulation may be provided in any form in accordance with the present disclosure. In one non-limiting example, the stimulation may include one or more current pulses, one or more voltage pulses, combinations thereof, or the like. The step of stimulation may be advantageous for assessing the updated signal at one or more measurement locations and/or between two or more measurement locations in the presence of background noise and/or local physiological activity.

In aspects, the method may include monitoring one or more remote physiological parameters in accordance with the present disclosure at a remote location (e.g. an alternative vessel, an organ, a ganglion, a nerve, etc.) substantially removed from the immediate vicinity of the vessel to determine an updated remote physiological signal and/or reference remote physiological signal.

Some non-limiting examples of remote physiological parameters that may be monitored include water concentration, tone, blood oxygen saturation of local tissues, evoked potential, stimulation/sensing of nervous activity, electromyography, temperature, blood pressure, vasodilation, vessel wall stiffness, muscle sympathetic nerve activity (MSNA), central sympathetic drive (e.g. bursts per minute, bursts per heartbeat, etc.), tissue tone, blood flow (e.g. through an artery, through a renal artery), a blood flow differential signal (e.g. a significantly abnormal and or sudden change in blood flow within a structure of the body, a vessel, an organ, etc.), blood perfusion (e.g. to an organ, an eye, etc.), a blood analyte level (e.g. a hormone concentration, norepinephrine, catecholamine, renin, angiotensin II, an ion concentration, a water level, an oxygen level, etc.), nerve traffic (e.g. post ganglionic nerve traffic in the peroneal nerve, celiac ganglion, superior mesenteric ganglion, aorticorenal ganglion, renal ganglion, and/or related nervous system structures), combinations thereof, and the like.

The updated remote physiological signal and/or reference remote physiological signal may be combined and/or compared with one or more reference signals, and/or one or more updated signals in order to determine the extent of completion, as part of a decision making process, and/or as part of a surgical control system (i.e. so as to determine whether to continue with, stop, or alter the surgical procedure).

The method may include selecting a surgical location. The step of selection may depend upon one or more monitoring steps, proximity to an alternative surgical location (i.e. perhaps a previously treated surgical location, etc.).

In aspects, the method may include sweeping the lumen while monitoring in order to localize one or more anatomical sites of interest, one or more regions of abnormal activity, etc.

In aspects, the steps of monitoring may be completed sequentially. Alternatively, additionally, or in combination, the steps of monitoring may be effectively continuously applied through the procedure. The comparison may be made using one or more data points obtained from one or more steps of monitoring. The comparison may be made via algorithmic combination of one or more measurements.

In aspects, the step of monitoring may be used to extract one or more electrophysiological parameters during a first period and monitoring an applied field (i.e. as caused by a stimulation and/or ablation event) during a second period.

In aspects, the method may include generating a topographical map from the one or more measurements (e.g. from one or more of the signals). The method may include determining a topographical map of physiological functionality in the vicinity of the surgical site derived from one or more of the physiological signals. The method may include updating the topographical map after the step of performing at least a portion of the surgical procedure. The method may include generating the map during a sweeping process (i.e. a longitudinal sweep, a circumferential sweep, a helical sweep, etc.).

In aspects, the method may include placement of a plurality of surgical tools, one or more surgical tools (i.e. a procedural tool) placed so as to access one or more of the surgical locations, and one or more surgical tools (i.e. a monitoring tool) placed so as to access one or more of the monitoring locations. In one non-limiting example, a procedural tool may be placed in a first vessel (e.g. a renal artery, a left renal artery, etc.) and a monitoring tool may be placed into a second vessel (e.g. an opposing renal artery, a right renal artery, a femoral artery, an iliac artery, etc.). Thus, the monitoring tool may be used to monitor one or more of the measurement locations in the second vessel. The procedural tool may be used to surgically treat one or more surgical locations in the first vessel. Additionally, alternatively, or in combination, the procedural tool may monitor one or more monitoring locations in the first vessel, perhaps in combination with monitoring performed in the second vessel by the monitoring tool.

In aspects, the method may be performed with one or more surgical tools in accordance with the present disclosure.

One or more steps of monitoring may be performed with one or more sensing tips in accordance with the present disclosure.

One or more steps of performing at least a portion of the surgical procedure may be performed with one or more sensing tips in accordance with the present disclosure.

In one non-limiting example of a method for RF ablating tissue, the local tissue tone may be measured before, during, between individual RF pulses, and/or after a train of RF pulses. As the local tissue tone changes during application of the RF pulses, the tonal changes may be used to determine the extent of the therapy. As the RF ablation process is applied to the adjacent tissues (perhaps via one or more sensing tips), the tonal measurements (as determined by one or more sensing tips, perhaps the same tip through which the RF signal may be applied) may be monitored to determine an extent of completion of the procedure. Such an approach may be advantageous as the tonal measurement techniques may not be significantly affected by the local RF currents associated with the RF ablation procedure.

In aspects, an interventionalist/proceduralist may insert a catheter in accordance with the present disclosure into the aorta from either the superior or inferior approach (brachial or femoral arteries) and selectively cannulate the renal artery. In aspects, a guiding catheter may be used for this purpose. In aspects, a microsurgical tool in accordance with the present disclosure may be placed through the guiding catheter. In aspects, one or more regions of the microsurgical tool may be deployed thus allowing one or more electrodes included therein to bias against the lumen of the renal artery. Such a configuration may be advantageous to establish excellent mechanical and electrical contact with the walls of the renal artery.

In aspects, the electrodes may be made to puncture the vessel wall from the lumen side. The electrodes may be expandable and/or retractable, exiting in a stable pattern of 1 to 6, or more microfingers that permit stability and counter-opposition force to cause penetration of one or more of the electrodes into the intima, media, or adventitia of the lumen (i.e. artery, vein, etc.) to be measured. In aspects, one or more electrodes may be configured for microscopic or macroscopic spatial recording. Following a suitable period of recording, the device may be withdrawn into the guiding catheter and removed from the body.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. A microsurgical tool for monitoring electrophysiological activity within the vicinity of a lumen, the microsurgical tool comprising:
   a microfinger having a substantially elongate structure configured so as to bias a region thereof against a wall of the lumen upon deployment within the lumen;
   a plurality of sensing tips electrically and mechanically coupled to the microfinger in the vicinity of the region, configured to interface with the wall of the lumen, a given one of the sensing tips configured:
   to measure electrophysiological activity within the vicinity of the lumen; and
   to convey, to an extracorporeal system, one or more electrophysiological signals associated with the measured physiological activity within the vicinity of the lumen; and
   a microcircuit electrically coupled to the given sensing tip and attached to the microfinger proximate to the given sensing tip such that, upon deployment of the microfinger within the lumen, the microcircuit is positioned in the lumen;
   wherein the microcircuit is configured to condition the electrophysiological signals sensed by the given sensing tip within the lumen prior to conveying the electrophysiological signals outside the lumen to the extracorporeal system;
   wherein conditioning the electrophysiological signals sensed by the given sensing tip comprises at least one of: converting the electrophysiological signals into digital form; and amplifying the electrophysiological signals;
   wherein the given sensing tip comprises a first core flexure and at least a second core flexure;
   wherein the first core flexure and the second core flexure each comprise at least one region covered with an insulating layer and at least one exposed region;
   wherein the first core flexure comprises a first exposed region providing a first electrode at a tip region of the given sensing tip;
   wherein the second core flexure comprises a second exposed region providing at least a second electrode at a shank region of the given sensing tip;

wherein a portion of the insulating layer extends between the first and second exposed regions; and wherein the microcircuit is configured to utilize electrophysiological signals measured by the first electrode and the second electrode to monitor neural activity differences between the tip region and the shank region of the given sensing tip.

2. The microsurgical tool in accordance with claim 1, wherein the electrophysiological signals are related to one or more of water concentration, tone, evoked potential, remote stimulation of nervous activity, an electromyographic signal [EMG], a mechanomyographic signal [MMG], a local field potential, an electroacoustic event, vasodilation, vessel wall stiffness, muscle sympathetic nerve activity [MSNA], central sympathetic drive, tissue tone and nerve traffic.

3. The microsurgical tool in accordance with claim 1, wherein the microfinger is configured so as to substantially maintain contact with the wall of the lumen while it is swept longitudinally down the lumen and/or circumferentially around the lumen.

4. The microsurgical tool in accordance with claim 1, wherein the microfinger is configured so as to substantially maintain a constant force against the wall of the lumen during relative movement there between.

5. The microsurgical tool in accordance with claim 1, wherein the microfinger has a characteristic width of less than 150 um, less than 100 um, less than 75 um, less than 50 um, less than 25 um, less than 10 um, or less than 5um.

6. The microsurgical tool in accordance with claim 1 comprising a plurality of microfingers, each microfinger configured so as to substantially independently bias against the wall of the lumen upon deployment.

7. The microsurgical tool in accordance with claim 6, wherein a plurality of microfingers are configured to form a cage, a mesh, or a stent-like structure.

8. The microsurgical tool in accordance with claim 6, wherein each microfinger is configured so as to independently maintain contact with the wall during relative movement there between.

9. The microsurgical tool in accordance with claim 8, wherein one or more of the microfingers are configured to convey signals in the presence of the relative movement.

10. The microsurgical tool in accordance with claim 1, wherein the given sensing tip comprises a needle electrode, the microfinger configured to plunge the needle electrode into the wall of the lumen upon deployment.

11. The microsurgical tool in accordance with claim 1, wherein the microfinger comprises an active material element configured to alter a contact force between the given sensing tip and the wall upon receipt of a control signal.

12. The microsurgical tool in accordance with claim 11, wherein the given sensing tip comprises a force sensor configured to measure a change in the contact force.

13. The microsurgical tool in accordance with claim 12, wherein the given sensing tip further comprises a strain sensor, and wherein the given sensing tip is configured to combine one or more force sensing signals obtained from the force sensor and one or more strain sensing signals obtained from the strain sensor to generate a mechanomyographic (MMG) signal.

14. The microsurgical tool in accordance with claim 1, wherein the first exposed region of the first core flexure is configured so as to substantially embed the given sensing tip into the wall of the lumen.

15. The microsurgical tool in accordance with claim 1, wherein the second exposed region of the second core flexure is oriented to one side of a neutral axis of the second core flexure of the given sensing tip so as to substantially maintain a constant force against the wall of the lumen during relative movement there between.

16. The microsurgical tool in accordance with claim 1, wherein the microfinger is part of a plurality of microfingers forming a longitudinal wire cage configured to maintain contact with the wall of the lumen without inhibiting flow of fluids through the lumen.

17. The microsurgical tool in accordance with claim 16, wherein the microsurgical tool further comprises a guidewire configured to assist with guiding the longitudinal wire cage to a target region within the lumen.

18. The microsurgical tool in accordance with claim 17, wherein the microsurgical tool further comprises a distal ringlet configured to accommodate passage of the guidewire through the longitudinal wire cage.

19. The microsurgical tool in accordance with claim 1, wherein the microfinger comprises a radially biased flexural spring.

20. The microsurgical tool in accordance with claim 1, wherein the microfinger is configured so as to be deployed from a delivery catheter and at least a portion of the delivery catheter has a diameter less than 3 mm.

21. The microsurgical tool in accordance with claim 1, wherein the microcircuit is embedded into the substantially elongate structure of the microfinger.

22. The microsurgical tool in accordance with claim 1, wherein the sensing tip comprises a compliance sensor configured to generate a tissue tone signal.

23. The microsurgical tool in accordance with claim 1, wherein the given sensing tip further comprises a flex circuit comprising a plurality interconnects.

24. The microsurgical tool in accordance with claim 1, wherein the first core flexure and the second core flexure are surrounding by a same insulating layer.

* * * * *

UNITED STATES PATENT AND TRADEMARK OFFICE
CERTIFICATE OF CORRECTION

PATENT NO.        : 10,470,684 B2
APPLICATION NO.   : 14/374466
DATED             : November 12, 2019
INVENTOR(S)       : Landy Toth et al.

Page 1 of 1

It is certified that error appears in the above-identified patent and that said Letters Patent is hereby corrected as shown below:

In the Claims

Claim 5, Column 51, Line 28 please delete "Sum" and insert -- 5um --

Signed and Sealed this
Third Day of March, 2020

Andrei Iancu
*Director of the United States Patent and Trademark Office*